United States Patent
Lindner et al.

(10) Patent No.: US 9,718,878 B2
(45) Date of Patent: Aug. 1, 2017

(54) KIT FOR DETECTING CTHRC1 IN A SAMPLE

(75) Inventors: Volkhard Lindner, South Portland, ME (US); Ilka Pinz, Limington, ME (US); Julia Patrizia Stohn, Biddeford, ME (US)

(73) Assignee: Maine Medical Center, Scarborough, ME (US)

( * ) Notice: Subject to any disclaimer, the term of this patent is extended or adjusted under 35 U.S.C. 154(b) by 96 days.

(21) Appl. No.: 13/578,102

(22) PCT Filed: Feb. 10, 2011

(86) PCT No.: PCT/US2011/024380
§ 371 (c)(1),
(2), (4) Date: Oct. 30, 2012

(87) PCT Pub. No.: WO2011/100453
PCT Pub. Date: Aug. 18, 2011

(65) Prior Publication Data
US 2013/0059786 A1 Mar. 7, 2013

Related U.S. Application Data

(60) Provisional application No. 61/303,015, filed on Feb. 10, 2010, provisional application No. 61/419,658, filed on Dec. 3, 2010.

(51) Int. Cl.
*C07K 16/18* (2006.01)
*A61K 38/17* (2006.01)
*C07K 14/47* (2006.01)
*C07K 14/78* (2006.01)
*G01N 33/53* (2006.01)
*G01N 33/577* (2006.01)
*G01N 33/68* (2006.01)

(52) U.S. Cl.
CPC .......... *C07K 16/18* (2013.01); *A61K 38/1709* (2013.01); *C07K 14/4703* (2013.01); *C07K 14/78* (2013.01); *C07K 2317/34* (2013.01); *G01N 33/53* (2013.01); *G01N 33/577* (2013.01); *G01N 33/68* (2013.01)

(58) Field of Classification Search
None
See application file for complete search history.

(56) References Cited

U.S. PATENT DOCUMENTS

2005/0147602 A1* 7/2005 Lindner .................... 424/130.1

FOREIGN PATENT DOCUMENTS

| WO | WO-2006098758 A2 | 9/2006 |
| WO | WO-2007/090076 A2 | 8/2007 |
| WO | WO-2009/057849 A1 | 5/2009 |

OTHER PUBLICATIONS

LeClair et al (2008. Arterioscler Thromb Vasc Biol. 28: 1332-1338).*
Benjamini et al, 1991. Immunology: A Short Course, 2nd edition, p. 40 only.*
Tang L. et al. "Aberrant expression of collagen triple helix repeat containing 1 in human solid cancers." Clin Cancer Res. Jun. 15, 2006;12(12):3716-22.
International Search Report and Written Opinion for PCT/US2011/024380 issued and mailed Oct. 18, 2011.

* cited by examiner

*Primary Examiner* — Zachary Howard
(74) *Attorney, Agent, or Firm* — Mintz Levin Cohn Ferris Glovsky and Popeo, P.C.

(57) ABSTRACT

The invention provides methods for the treatment of coronary heart disease, peripheral vascular disease, stroke, and ischemia featuring agents that interfere with the expression or activity of Cthrc1. The invention also provides the use of Cthrc1 peptide as a therapeutic agent for the treatment of acute or chronic cardiac deficiencies. The invention further provides detection and monitoring of Cthrc1 peptide in blood or serum to assess or monitor cardiac function.

3 Claims, 26 Drawing Sheets

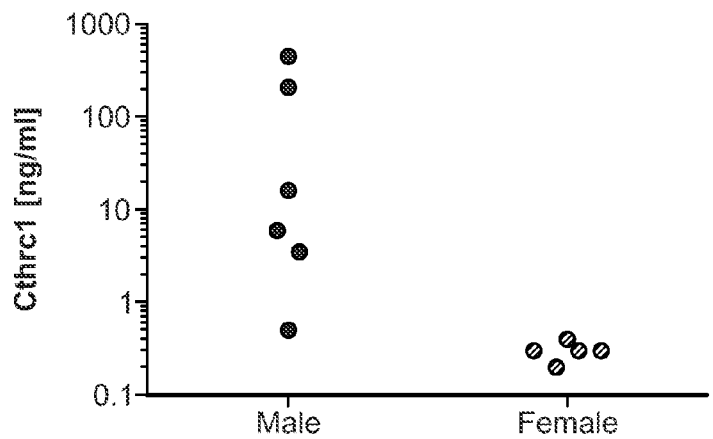
FIG. 3
Pharmacokinetics of Cthrc1 in Plasma
6μg of $^{125}$I-Cthrc1 were infused into the left carotid artery.
Plasma samples were obtained at the indicated times.
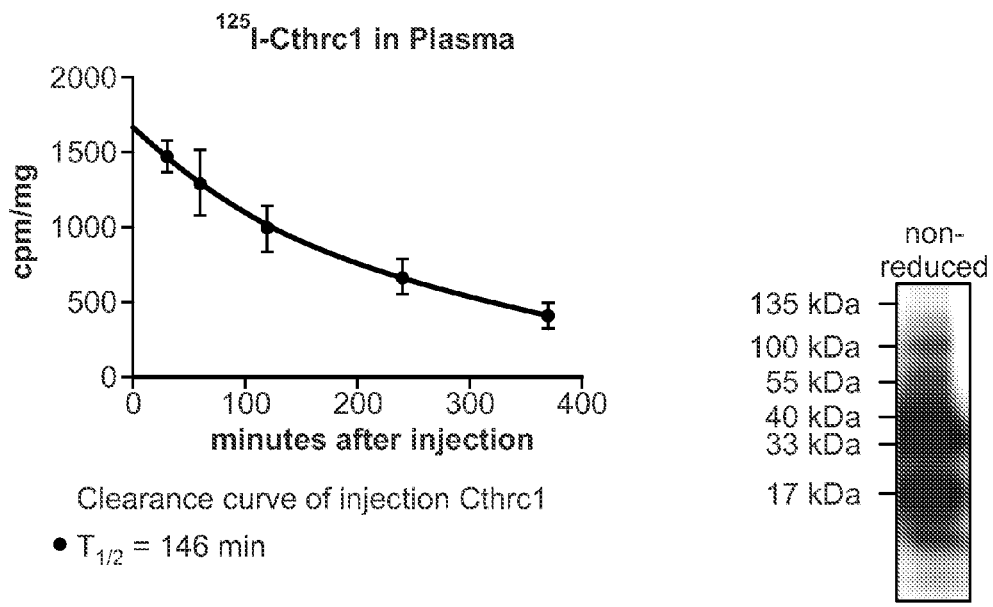
Clearance curve of injection Cthrc1
● $T_{1/2}$ = 146 min
FIG. 4A
Plasma sample after 30 min
Plasma was subject to SDS-PAGE followed by autoradiography of the gel.
FIG. 4B

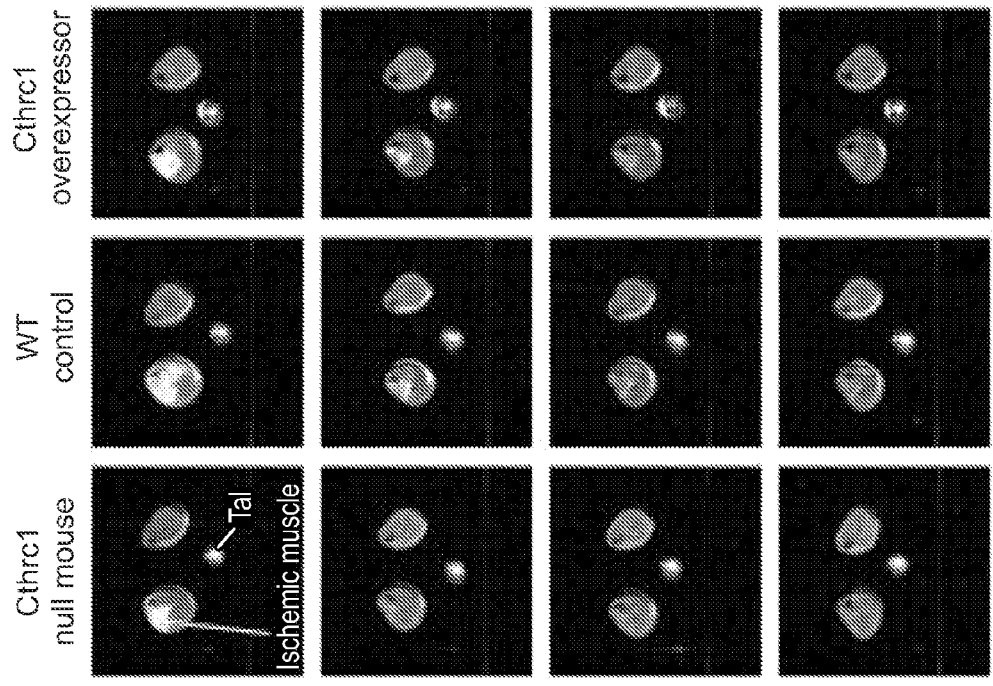
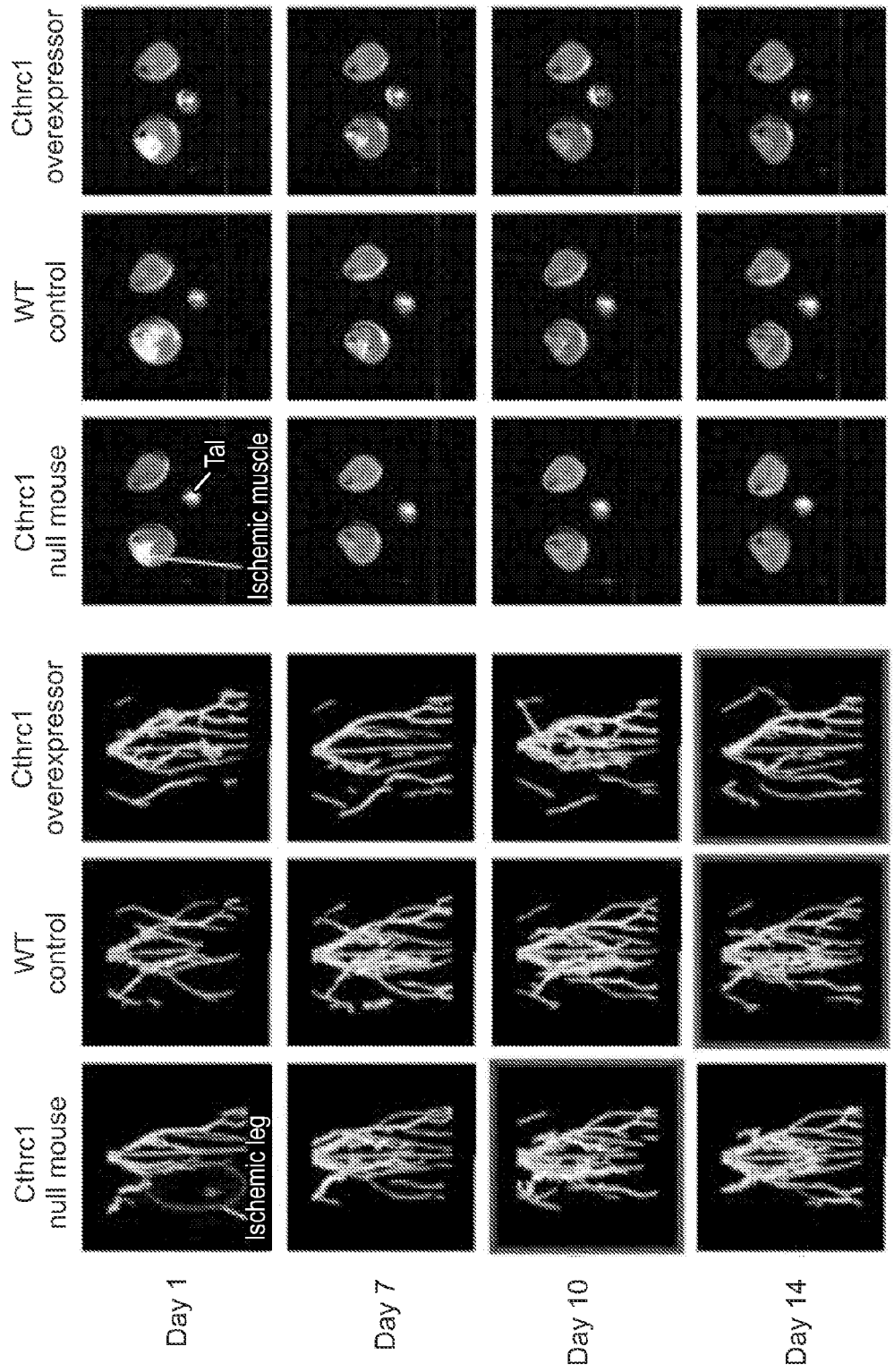

Liver
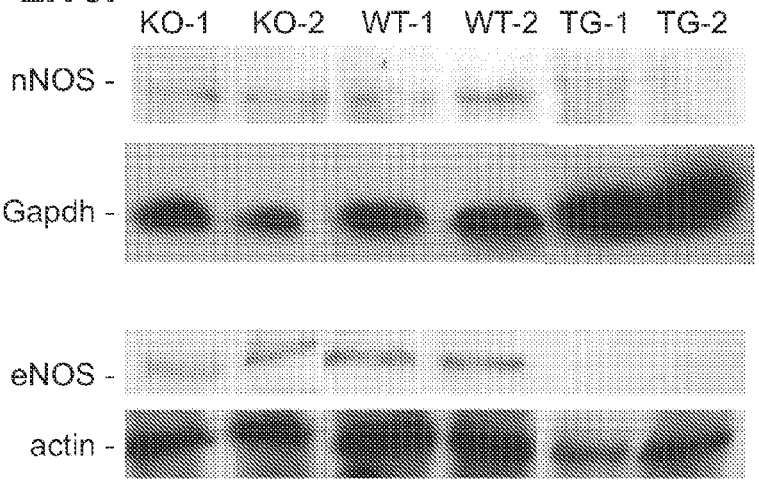
Brain
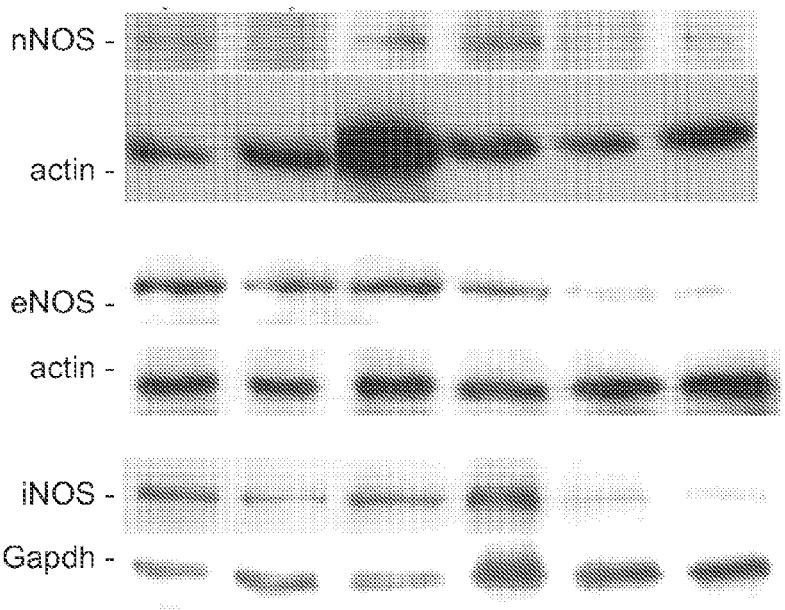
Aorta
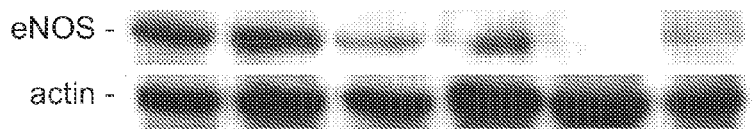
Heart
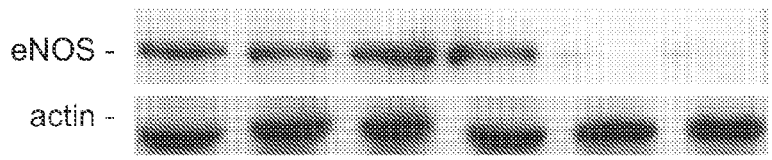
FIG. 9A

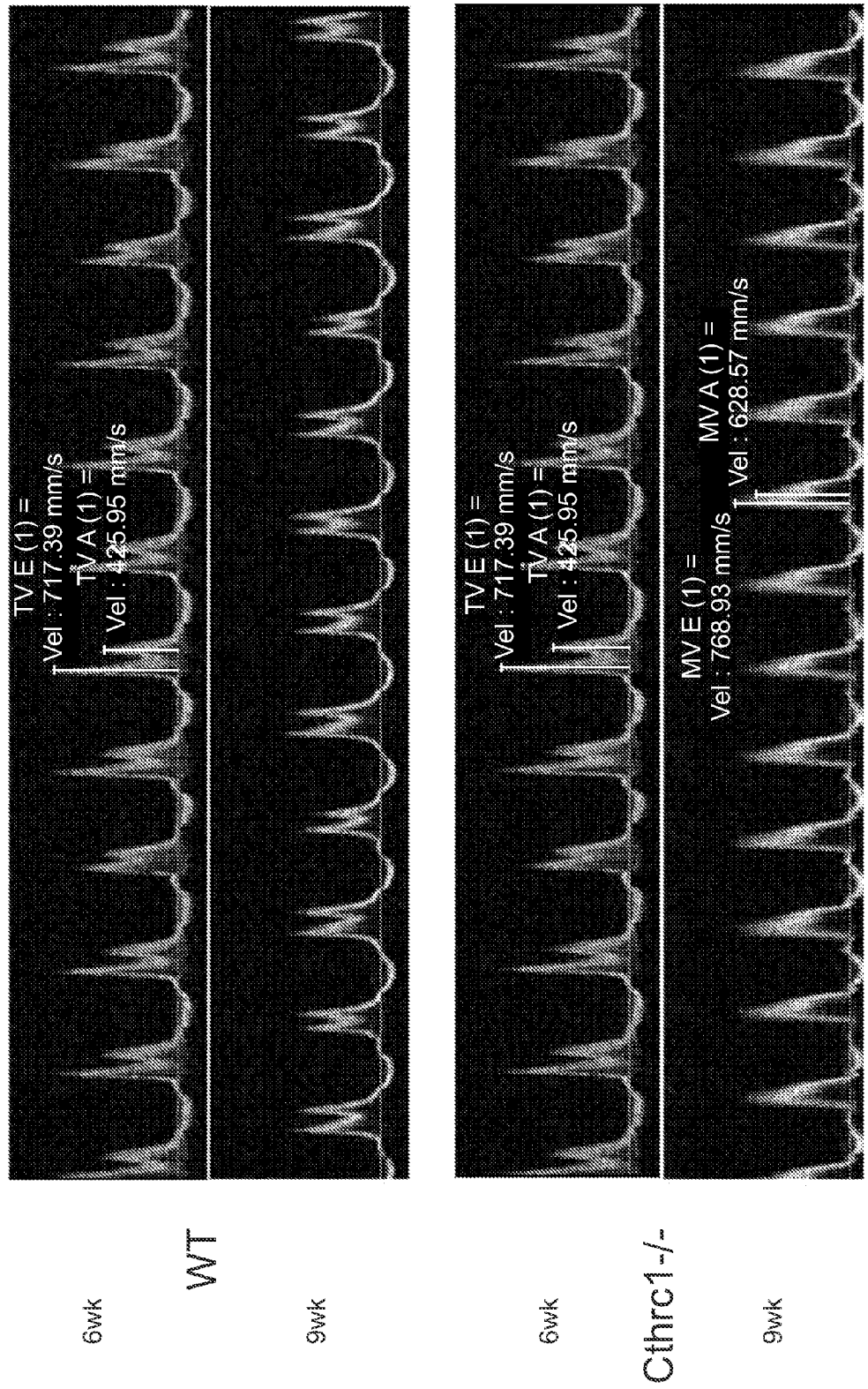

FIG. 14A

```
LOCUS       AAQ89273                 243 aa            linear   PRI
03-OCT-2003
DEFINITION  CTHRC1 [Homo sapiens].
ACCESSION   AAQ89273
VERSION     AAQ89273.1  GI:37182946
DBSOURCE    accession AY358914.1
SOURCE      Homo sapiens (human)
  1 mrpqgpaasp qrlrglllll llqlipapssa seipkgkqka qlrqrevvdl yngmclqgpa
 61 gvpgrdgspg anvipgtpgi pgrdgfkgek geclresfee swtpnykqcs wsslnygidl
121 gkiaectftk mrsnsalrvl fsgslrlkcr naccqrwyft fngaecsgpl pieaiiyldq
181 gspemnstin ihrtssvegl cegigaglvd vaiwvgtcsd ypkgdastgw nsvsriiee
241 lpk
```

FIG. 14B

```
LOCUS       AY358914                 732 bp    mRNA    linear
PRI 03-OCT-2003
DEFINITION  Homo sapiens clone DNA76393 CTHRC1 (UNQ762) mRNA,
            complete cds.
ACCESSION   AY358914 REGION: 138..869
VERSION     AY358914.1  GI:371182945
SOURCE      Homo sapiens (human)

1 atgcgacccc agggcccgc cgcctccccg cagcggctcc gcggcctcct gctgctcctg
 61 ctgctgcagc tgcccgcgcc gtcgagcgcc tctgagatcc gtcgagcgcc ccaaggggaa gcaaaaggcg
121 cagctccggc agagggaggt ggtggacctg tataatggaa tgtgcttaca agggccagca
181 ggagtgcctg gtcgagacgg gagccctggg gccaatgtta ttccgggtac acctgggatc
241 ccaggtcggg atggattcaa aggagaaaag ggggaatgtc tgagggaaag ctttgaggag
301 tcctggacac ccaactacaa gcagtgttca tggagttcat tgaattatgg catagatctt
```

FIG. 14C

```
361 gggaaaattg cggagtgtac atttacaaag atgcgttcaa atagtgtct aagagttttg
421 ttcagtggct cacttcggct aaaatgcaga aatgcatgct gtcagcgttg gtatttcaca
481 ttcaatggag ctgaatgttc aggacctctt cccattgaag ctataattta tttggaccaa
541 ggaagccctg aaatgaattc aacaattaat attcatcgca cttcttctgt ggaaggactt
601 tgtgaagaa ttggtgctgg attagtggat gttgctatct gggttggcac ttgttcagat
661 tacccaaaag gagatgcttc tactgatgg aattcagttt ctcgcatcat tattgaagaa
721 ctaccaaaat aa
```

FIG. 14D

```
LOCUS       XP_001494121             244 aa            linear    MAM
11-JUL-2008
DEFINITION  PREDICTED: similar to collagen triple helix repeat
            containing 1
            [Equus caballus].
ACCESSION   XP_001494121
VERSION     XP_001494121.2  GI:194215028
  1 mrpgqpaaac sqrllglill lllqlrtpss asetpkgkqk allrqrevvd lyngmclqgp
 61 agvpgrdgsp gangipgtpg ipgrdgfkge kgeclretfe eswtpnykqc swsslnygid
121 lgkiaectft kmrsnsalrv lfsgslrlkc rnaccgrwyf tfngaecsgp lpieaiiyld
181 qgspelnsti nihrtssveg lcegigaglv diaiwvgtcs dypkgdastg wnsvsriiie
241 elpk
```

FIG. 14E

```
LOCUS       XM_001494071             735 bp    mRNA    linear   MAM
11-JUL-2008
DEFINITION  PREDICTED: Equus caballus similar to collagen triple
helix repeat
            containing 1 (LOC100062543), mRNA.
ACCESSION   XM_001494071
VERSION     XM_001494071.2  GI:194215027
KEYWORDS    .
SOURCE      Equus caballus (horse)

1 atgcgccccc agggccccgc cgccgcctgc cgccgcctgc tcgcagcggc tcctcggtct gctgctgctc
 61 ctgctgctgc agctgcggac gccgtcgagc gcctccgaga gcctccgaga cccccaaggg gaagcaaaag
121 gcgctgctcc ggcagaggga ggtggtggac ctgtataatg gaatgtgctt acaagggcct
181 gcaggggtgc cagggcgaga tgggagccct ggggccaatg gcattcctgg taccccctggg
```

FIG. 14F

```
241 atcccaggtc gggatggatt caaaggagaa aaggggggaat gcctgaggga aaccttcgag
301 gagtcgtgga cacctaacta caagcagtgt tcgtggagtt cgctgaatta tggcatagat
361 cttgggaaaa ttgcggagtg tacatttaca aagatgcgtt cgaacagtgc tctgagagtt
421 ttgttcagtg gctcgcttcg gttaaaatgc agaaacgcat gctgtcagcg ttggtatttc
481 acgttcaatg gagctgaatg ttcaggacct cttcccattg aagctataat ttattggac
541 caaggaagcc cagaactgaa ttcaacaatt aatattcatc gcacttcttc tgtgaagga
601 ctttgtgaag gaattggtgc cggattagtg gatattgcta tctggttgg tacttgttcc
661 gactacccaa aaggagacgc ctctactgga tggaattcag tgtcccgaat cattatcgaa
721 gaactaccaa aataa
```

FIG. 14G

```
LOCUS       EDM16354                 277 aa            linear   ROD
20-JUN-2007
DEFINITION  collagen triple helix repeat containing 1 [Rattus
            norvegicus].
ACCESSION   EDM16354
VERSION     EDM16354.1  GI:149066481
DBSOURCE    accession CH473950.2

1 mrpaaelgqt lsraglcrpl clllcasqlp htmhpqgraa spqlliglfl vlllllqlsa
 61 pssasenpkv kqkalirqre vvdlyngmcl qgpagvpgrd gspgangipg tpgipgrdgf
121 kgekgeclre sfeeswtpny kqcswsslny gidlgkiaec tftkmrsnsa lrvlfsgslr
181 lkcrnaccqr wyffngaec sgplpieaii yldqgspeln stinihrtss veglcegiga
241 glvdvaiwvg tcsdypkgda stgwnsvsri iieelpk
```

FIG. 14H

```
LOCUS       AAI31908                 245 aa            linear   ROD
06-DEC-2007
DEFINITION  Collagen triple helix repeat containing 1 [Mus musculus].
ACCESSION   AAI31908
VERSION     AAI31908.1  GI:124298034
DBSOURCE    accession BC131907.1
KEYWORDS    MGC.
SOURCE      Mus musculus (house mouse)

1 mhpqgraapp qlilgifivl lillqlsaps sasenpkvkq kalirqrevv dlyngmclqg
 61 pagvpgrdgs pgangipgtp gipgrdgfkg ekgeclresf eeswtpnykq cswsslnygi
121 dlgkiaectf tkmrsnsalr vlfsgslrlk crnaccqrwy ftfngaecsg plpieaiiyl
181 dqgspelnst inihrtssve glcegigagl vdvaiwvgtc sdypkgdast gwnsvsriii
241 eelpk
```

FIG. 14I

```
LOCUS       XP_001156837             198 aa            linear   PRI
15-SEP-2006
DEFINITION  PREDICTED: collagen triple helix repeat containing 1
            isoform 1 [Pan troglodytes].
ACCESSION   XP_001156837
VERSION     XP_001156837.1  GI:114621227
DBSOURCE    REFSEQ: accession XM_001156837.1
KEYWORDS    .
SOURCE      Pan troglodytes (chimpanzee)

1 mrpqgpaasp qrlrglllll llqlpapssa seipkgkqka qlrqrevvdl yngmclqgpa
 61 gvpgrdgspg angipgtpgi pgrdgfkgek geclresfee swtpnykqcs wsslnygidl
121 gkiaectftk mrsnsalrvl fsgslrlkcr naccqrwyft fngaecsgpl pieaiiyldq
181 gspemnstin ihrtssgm
```

FIG. 14J

```
LOCUS       XP_001085750             243 aa            linear   PRI
14-JUN-2006
DEFINITION  PREDICTED: similar to collagen triple helix repeat
            containing 1 isoform 2 [Macaca mulatta].
ACCESSION   XP_001085750
VERSION     XP_001085750.1  GI:1090087181
DBSOURCE    REFSEQ: accession XM_001085750.1
KEYWORDS    .
SOURCE      Macaca mulatta (rhesus monkey)

1 mrpqgpaasp qrlrglllll llqlpapssa seipkgkqka qlrqrevvdl yngmclqgpa
 61 gvpgrdgspg angipgtpgi pgrdgfkgek geclresfee swtpnykqcs wsslnygidl
121 gkivectftk mrsnsalrvl fsgslrlkcr naccqrwyft fngaecsgpl pieaiiyldq
181 gspemnstin ihrtssvegl cegigaglvd vaiwvgtcsd ypkgdastgw nsvsriiiee
241 lpk
```

FIG. 14K

```
LOCUS       AY358914                 732 bp    mRNA    linear   PRI
03-OCT-2003

DEFINITION  Homo sapiens clone DNA76393 CTHRC1 (UNQ762) mRNA,
            complete cds.

ACCESSION   AY358914 REGION: 138..869

VERSION     AY358914.1  GI:37182945

KEYWORDS    FLI_CDNA.

SOURCE      Homo sapiens (human)

1 atgcgacccc agggcccgc cgcctccccg cagcggctcc gcggcctcct gctgctcctg
  61 ctgctgcagc tgcccgcgcc gtcgagcgcc tctgagatcc ccaaggggaa gcaaaaggcg
 121 cagctccggc agagggaggt ggtggacctg tataatggaa tgtgcttaca agggccagca
 181 ggagtgcctg gtcgagacgg gagccctggg gccaatgtta ttccgggtac acctgggatc
 241 ccaggtcggg atggattcaa aggagaaaag ggggaatgtc tgagggaaag ctttgaggag
```

FIG. 14L

```
301 tcctggacac ccaactacaa gcagtgttca tggagttcat tgaattatgg catagatctt
361 gggaaaattg cggagtgtac atttacaaag atgcgttcaa atagtgctct aagagttttg
421 ttcagtggct cacttcggct aaaatgcaga aatgcatgct gtcagcgttg gtattcaca
481 ttcaatggag ctgaatgttc aggacctctt cccattgaag ctataattta tttggaccaa
541 ggaagccctg aaatgaattc aacaattaat attcatcgca cttcttctgt ggaaggactt
601 tgtgaaggaa ttggtgctgg attagtggat gttgctatct gggttggcac ttgttcagat
661 tacccaaaag gagatgcttc tactggatgg aattcagttt ctcgcatcat tattgaagaa
721 ctaccaaaat aa
```

KIT FOR DETECTING CTHRC1 IN A SAMPLE

This application is the U.S. national phase application, pursuant to 35 U.S.C. §371, of PCT International Application Ser. No. PCT/US2011/024380, filed Feb. 10, 2011, designating the United States and published in English as publication WO 2011/100453 A2 on Aug. 18, 2011, which claims priority to U.S. Provisional Application No. 61/303,015, filed Feb. 10, 2010, and 61/419,658, filed Dec. 3, 2010, the entire contents of each of which are incorporated herein by reference.

GOVERNMENT SUPPORT

This invention was made with government support under grant number HL069182 awarded by the National Institutes of Health and under grant number F32HL091615 awarded by the National Heart, Lung, and Blood Institute. The government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 25, 2012, is named 85594.txt and is 18,382 bytes in size.

BACKGROUND

Blood vessels can adjust to altered hemodynamic situations by changing their diameter. For example, a reduction or cessation of blood flow through the common carotid artery leads to constrictive remodeling of the vessel with a decrease in total cross-sectional vessel area and a decrease in lumen area. Conversely, during the development of atherosclerotic plaques in arteries a loss of lumen area is initially counteracted via the process of outward remodeling of the vessel, so that the lumen area can be maintained despite an increase in plaque volume.

However, with continued plaque growth in coronary heart disease and peripheral vascular disease there is limited ability for compensatory outward remodeling of the vessel. Thus, the vessel lumen decreases and tissue perfusion decreases. Many approaches including those using angiogenic growth factors to promote vascularization of ischemic tissues have failed in clinical trials.

Heart failure is a consequence of impaired cardiac function and therapeutic options to improve cardiac performance are limited. Most inotropic factors also increase heart rate thereby increasing the oxygen requirements of the myocardium, which can exacerbate existing ischemic conditions even further. Agents that can promote cardiac perfusion and increase contractile performance without affecting heart rate would be highly desirable from a therapeutic point of view.

Thus, there is a need to develop safe and efficacious approaches for the treatment of coronary heart disease, peripheral vascular disease, and cardiac failure.

SUMMARY OF THE INVENTION

As described below, the present invention features compositions and methods for treating and prevention coronary heart disease, peripheral vascular disease, and cardiac failure. In one embodiment, the invention provides compositions and methods for inhibiting the expression or activity of collagen triple helix repeat containing-1 (Cthrc1) protein.

In one aspect, the invention provides a method of increasing blood vessel formation or remodeling in a subject in need thereof, the method involving administering to the subject an agent that selectively reduces the expression or activity of Cthrc1 relative to a reference, thereby increasing blood vessel formation or remodeling in the subject.

In another aspect, the invention provides a method of increasing blood vessel diameter, the method involving contacting a blood vessel cell or endothelial cell with an agent that selectively reduces the expression or activity of Cthrc1, thereby increasing blood vessel diameter.

In yet another aspect, A method of treating or preventing coronary heart disease, peripheral vascular disease, stroke, or ischemia in a subject in need thereof, the method involving administering to the subject an agent that selectively reduces the expression or activity of Cthrc1, thereby increasing blood vessel formation or remodeling in the subject.

In still another aspect, the invention provides for uses of an agent that selectively reduces the expression or activity of Cthrc1 in a cell for the preparation of a pharmaceutical composition or medicament for the treatment of coronary heart disease, peripheral vascular disease, stroke, ischemia, or a symptom thereof. In various embodiments of any of the aspects delineated herein, the pharmaceutical composition for the treatment of coronary heart disease, peripheral vascular disease, stroke, ischemia, or a symptom thereof, contains an effective amount of an agent that selectively reduces the expression or activity of Cthrc1 in a cell.

In another aspect, the invention provides a kit for treating coronary heart disease, peripheral vascular disease, stroke, or ischemia comprising an effective amount of an agent that selectively reduces the expression or activity of Cthrc1 in a cell and instructions for using the kit to treat coronary heart disease, peripheral vascular disease, stroke, or ischemia.

In various embodiments of any of the aspects delineated herein, the agent is an inhibitory nucleic acid molecule that is complementary to at least a portion of a Cthrc1 nucleic acid molecule. In various embodiments the inhibitory nucleic acid molecule is one or more of an antisense molecule, an siRNA, and an shRNA. In various embodiments of any of the aspects delineated herein, the agent is an antibody or fragment thereof that selectively binds to the Cthrc1 polypeptide. In various embodiments, the antibody is a monoclonal or polyclonal antibody.

In various embodiments of any of the aspects delineated herein, the subject has, has had, or is at risk of having coronary heart disease, peripheral vascular disease, stroke, or ischemia. In various embodiments of any of the aspects delineated herein, the method or pharmaceutical composition increases vascularization, lumen diameter, or arteriogenesis. In various embodiments of any of the aspects delineated herein, the expression or activity of Cthrc1 is selectively reduced in a blood vessel cell, mural cell, pericyte, or adventitia cell. In various embodiments of any of the aspects delineated herein, the agent selectively reduces said expression by at least about 10% relative to the expression of Cthrc1 in an untreated control cell.

In one aspect, the invention provides methods for increasing cardiac function or treating or preventing cardiac insufficiency in a subject by administering a Cthrc1 protein to the subject or by increasing the expression or biological activity of Cthrc1 in the subject. In various embodiments of any of the aspects delineated herein, cardiac insufficiency can be a result of genetic predisposition, lifestyle, injury, or any combination thereof. Cardiac insufficiency can manifest as congestive heart failure, impaired cardiac function due to coronary heart disease, myocardial infarction, dilated cardiomyopathy, or any of a number of conditions related to heart disease in which result in inability of the heart to keep up with the demands on it and, specifically, failure of the heart to pump blood with normal efficiency. In certain embodiments, the method further includes diagnosing the subject as suffering from cardiac insufficiency. In certain embodiments, the method further includes monitoring the subject for a decrease in cardiac insufficiency.

In another aspect, the invention provides for uses of a Cthrc1 protein for preparation of a pharmaceutical composition or medicament for increasing cardiac function or treating cardiac insufficiency in a subject. In various embodiments of any of the aspects delineated herein, the pharmaceutical composition contains an effective amount of a Cthrc1 polypeptide. In various embodiments of any of the aspects delineated herein, the pharmaceutical composition increases cardiac function in a subject by at least about 10% relative to a reference. In various embodiments of any of the aspects delineated herein, cardiac insufficiency is any one or more of congestive heart failure, impaired cardiac function due to coronary heart disease, myocardial infarction, dilated cardiomyopathy, or a symptom thereof.

In yet another aspect, the invention provides methods for determining reduced cardiac function or measuring cardiac insufficiency in a subject by obtaining a subject sample, and detecting Cthrc1 level in the subject sample. The level is compared to levels present in a reference or control sample to determine if the level is normal (i.e., not associated with cardiac insufficiency) or abnormal (i.e., associated with cardiac insufficiency). The methods include monitoring a subject over time for changes in Cthrc1 levels as an indication of a change in cardiac function. Cthrc1 levels can be repeated at regular intervals (e.g., monthly, semi-annually, annually as part of a physical examination, etc.), or to determine changes in cardiac function in response to a specific event (e.g., surgery, new therapeutic regimen, etc.). Methods of detecting cardiac insufficiency can also include the use of any other diagnostic method or methods with the diagnostic methods provided herein. In various embodiments of any of the aspects delineated herein, the level of Cthrc1 is determined in a subject sample, for example in a tissue, for example cardiac tissue, or a body fluid, for example in blood, serum, or plasma. In certain embodiments, the detection method is an immunoassay.

In an additional aspect, the invention provides methods for screening for agents that bind a Cthrc1 binding protein. Screening methods include, for example, competition assays. Such methods include the steps of obtaining a Cthrc1 binding protein; contacting the Cthrc1 binding protein with Cthrc1 in a first sample under conditions to allow binding (e.g., physiological condition); and contacting Cthrc1 binding protein with Cthrc1 in a second sample in the presence of an agent under the same binding conditions as the first sample. Binding of Cthrc1 binding protein to Cthrc1 in the first sample is compared to binding of Cthrc1 binding protein to Cthrc1 in the second sample. If the agent alters (i.e., reduces or increases) the binding of the Cthrc1 binding protein to Cthrc1, the agent likely binds to either the Cthrc1 binding protein or Cthrc1 or both. Such an agent can be an agonist or antagonist of Cthrc1 activity.

In another aspect, the invention provides kits for performing an assay to detect Cthrc1 in a subject sample or performing any of the methods of the invention. In certain embodiments, the kit is an immunoassay.

The present application is related to U.S. Pat. No. 6,630,325; U.S. patent application Ser. Nos. 09/692,081, 10/045,992, 10/634,108, and 10/939,233; and U.S. Provisional Patent Application Ser. Nos. 60/503,933 and 60/504,107. The aforementioned applications are incorporated herein by reference in their entirety.

BRIEF DESCRIPTION OF THE FIGURES

FIG. 1A is a schematic of the wild-type allele and mutant allele with replacement of exons 2-4 with a PGK-neo cassette. FIG. 1B shows the results of ES cell targeting: Southern blot analysis of genomic DNA from ES cell clones showing a targeted clone.

FIG. 3 is a graph showing individual CTHRC1 levels detected in human plasma. ELISA plates were coated with rabbit monoclonal anti-Cthrc1 (clone Vli-42, 2.5 µg/ml), followed by addition of human plasma samples from healthy males and females. Captured CTHRC1 was then detected with mouse monoclonal anti-Cthrc1 (clone 16D4, 1 µg/ml). The graph shows concentrations of CTHRC1 found in human plasma samples in ng/ml.

FIG. 4A is a graph depicting the results of injecting recombinant purified Cthrc1 radiolabeled with $^{125}$I into Cthrc1$^{-/-}$ mice. Cthrc1 levels were determined by gamma counting and the half-life in circulation was calculated to be 146 minutes. FIG. 4B depicts the analysis of a plasma sample by SDS-PAGE under non-reducing conditions followed by autoradiography showed that the radiolabeled Cthrc1 circulates in the form of multimeric complexes.

FIG. 5A shows prominent Cthrc1 expression in pericytes of brain post capillary venules (inset—higher magnification view of venule with immunoreactive Cthrc1 in pericyte. Secretion of Cthrc1 into the lumen of the venule was observed (FIG. 5B). FIG. 5C shows that no immunoreactivity was observed in Cthrc1$^{-/-}$, thus, demonstrating specificity of the anti-Cthrc1 antibody. Prominent expression in cells surrounding the tunica media was also observed in larger vessels such as the aorta (Ao, FIG. 5D), the umbilical artery (FIG. 5E) and muscular veins (FIG. 5F). The closing ductus arteriosus (DA, FIG. 5D) showed Cthrc1 expression throughout the entire vessel wall. FIGS. 5G and 5H show expression in pericytes (arrowheads) surrounding endothelial cells (arrows) of postcapillary venules in a growing testicular tumor. Nuclear counterstain with hematoxylin.

FIGS. 7A and 7B depict representative MR angiograms (FIG. 7A) and MR images of calf tissue (FIG. 7B) showing the ischemic muscle (bright areas in the left calves). Cthrc1 null mice show larger blood vessel diameter in the angiograms compared to WT and Cthrc1 overexpressing mice. They are also able to re-connect the excised femoral artery 4 days sooner than wild-type (WT) and Cthrc1 overexpressing mice (red squares in (FIG. 7A)). In addition, this group re-establishes blood flow to the ischemic muscle area 7 days sooner than WT or Cthrc1 overexpressing mice. The bright muscle area in (FIG. 7B) has recovered within 7 days post surgery in Cthrc1$^{-/-}$ mice, suggesting collateral formation that is not detected by the MR angiography. Experiments repeated twice with similar results (n=3 animals per group).

FIG. 8A depicts T1 weighted images of WT and Cthrc1−/− livers show higher signal intensity in the vascular beds of Cthrc1−/− livers indicating dilated vessels in the mutants. FIG. 8B shows a three-dimensional reconstruction of the magnetic resonance angiograms with dilation of veins in the mutants. FIG. 8C is a series of photomicrographs showing that Histology of livers from WT and Cthrc1−/− mice revealed dilated hepatic veins and sinuses in the mutant mice (FIG. 9C, hematoxylin and eosin).

FIG. 9A depicts the inhibition of nitric oxide synthase isoforms in various tissues from two Cthrc1 overexpressing mice (TG-1 and TG-2).

FIG. 10A and FIG. 10B depict representative echocardiographic M-mode images and Doppler flow analysis at the mitral valve. Left panel: M-mode images of Cthrc1−/− mice at 11 weeks of age (bottom) show left ventricular dilatation as well as contractile dysfunction compared to matched wild type mice (top). Right panel: Flow measurements at the mitral valve show normal diastolic function at 6 weeks of age in the mutants. At 6 weeks of age the E/A ratio indicates diminished diastolic performance based on the missing or diminished A peak representing the atrial contraction.

FIG. 11A depicts a section of the heart atria from a one day old mouse with Cthrc1 detected by immunohistochemistry with anti-Cthrc1 Vli-77 (brown color). The myocardium of the left atrium (LA) reveals Cthrc1 expression. FIG. 11B depicts a higher magnification view of immunoreactive Cthrc1 expressed in the left atrial myocardium. FIG. 11C depicts a normal myocardium from a wild type mouse. FIG. 11D depicts the left ventricle from an 8 month old Cthrc1 null mouse showing extensive areas of cardiomyocyte degeneration with fibrosis. FIG. 11E and FIG. 11F depict Trichrome staining of diseased areas demonstrating fibrosis with collagen in blue.

FIG. 14A, FIG. 14B, FIG. 14C, FIG. 14D, FIG. 14E, FIG. 14F, FIG. 14G, FIG. 14H, FIG. 14I, FIG. 14J, FIG. 14K, and FIG. 14L depict representative Cthrc1 sequences.

DEFINITIONS

Figure 1A:
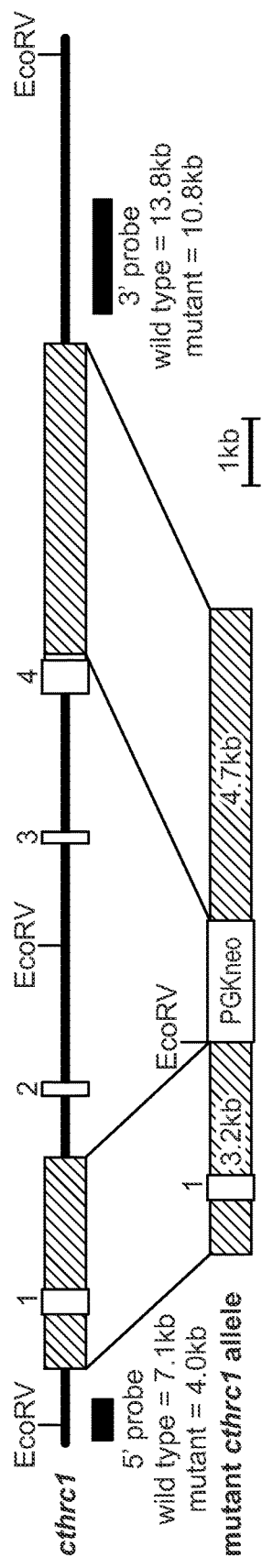
FIGS. 1A and 1B depicts the generation of Cthrc1 deficient mice.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "antibody" is meant any immunoglobulin polypeptide, or fragment thereof, having immunogen binding ability. As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies, and the like, as well as synthetic antigen-binding peptides and polypeptides, are also included. Non-human antibodies may be humanized by grafting non-human CDRs onto human framework and constant regions, or by incorporating the entire non-human variable domains. In certain preferred embodiments, humanized antibodies may retain non-human residues within the human variable region framework domains to enhance proper binding characteristics.

"Antigenic fragment" and the like are understood as at least that portion of a peptide capable of inducing an immune response in a subject, or being able to be specifically bound by an antibody raised against the antigenic fragment. Typically, antigenic fragments are at least 7 amino acids in length. Antigenic fragments can include deletions of the amino acid sequence from the N-terminus or the C-terminus, or both. For example, an antigenic fragment can have an N- and/or a C-terminal deletion of about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, or more amino acids. Antigenic fragments can also include one or more internal deletions of the same exemplary lengths. Antigenic fragments can also include one or more point mutations, particularly conservative point mutations. At least an antigenic fragment of protein can include the full length, wild-type sequence of the antigen. An antigenic fragment can include more than one potential antibody binding site. An antigenic fragment can be used to make antibodies for use in any of the methods provided herein.

By "blood vessel formation" is meant the dynamic process that includes one or more steps of blood vessel development and/or maturation, such as angiogenesis, arteriogenesis, vasculogenesis, formation of an immature blood vessel network, blood vessel remodeling, blood vessel stabilization, blood vessel maturation, blood vessel differentiation, or establishment of a functional blood vessel network.

By "blood vessel remodeling" or "vascular remodeling" is meant the dynamic process of blood vessel enlargement in shape and size to maintain the luminal orifice and blood flow. For example, vascular remodeling includes change in arterial size to adapt to plaque accumulation, effectively maintaining the lumen and blood flow to the myocardium.

As used herein, "binding" or "specific binding" is understood as having at least a $10^3$ or more, preferably $10^4$ or more, preferably $10^5$ or more, preferably $10^6$ or more preference for binding to a specific binding partner as compared to a non-specific binding partner (e.g., binding an antigen to a sample known to contain the cognate antibody). As the CTHRC1 protein is known to include collagen like sequences, an antibody specific to CTHRC1 is understood to bind CTHRC1 at least a $10^3$ or more, preferably $10^4$ or more, preferably $10^5$ or more, preferably $10^6$ or more preference for binding to a specific binding partner as compared to a mammalian collagen domain, preferably a human collagen domain (e.g., human collagen accession numbers include Accession No. AAA36358; BAA04809.1; CAA34683.1; Q02388.2) or a collagen repeat sequence (Collagen repeat sequences typically follows the pattern Gly-Pro-Y or Gly-X-Hyp, where X and Y may be any of various other amino acid residues).

By "Cthrc1 polypeptide" is meant a protein or fragment thereof having having at least about 85% (85%, 90%, 95%, 96%, 97%, 98%, 99% or 100%) amino acid identity to the amino acid sequence of Cthrc1 provided at GenBank Accession No. AAQ89273 that inhibits arteriogenesis or inhibits vascular remodeling.

By "Cthrc1 nucleic acid molecule" is meant a polynucleotide that encodes a Cthrc1 polypeptide.

By "Cthrc1 biological activity" is meant arteriogenesis activity, vascular remodeling activity, or inhibition of iNOS, inhibition of eNOS, coronary blood flow enhancing activity, or myocardial contractile function increasing activity.

By "cardiac function" is meant the biological function of cardiac tissue or heart (e.g., contractile function). Methods for measuring the biological function of the heart are standard in the art (e.g., Textbook of Medical Physiology, Tenth edition, (Guyton et al., W.B. Saunders Co., 2000) and are also described herein. By "increasing in cardiac function" is meant an increase in a biological function of the heart by at least about 5%, 10%, 15%, 20%, 30%, 40%, 50%, 60%, 70%, 80%, 90%, or even 100% relative to the biological function present in a naturally-occurring, corresponding cardiac tissue or heart.

As used herein, "cardiac insufficiency" is understood as any of a number of conditions related to heart disease in which result in inability of the heart to keep up with the demands on it and, specifically, failure of the heart to pump blood with normal efficiency. When this occurs, the heart is unable to provide adequate blood flow to other organs such as the brain, liver and kidneys. Insufficiency can be due to acute or chronic cardiac damage. Such conditions include, but are not limited to, congestive heart failure, impaired cardiac function due to coronary heart disease, myocardial infarction, dilated cardiomyopathy, etc.

By "control" or "reference" is meant a standard of comparison. As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g., β-galactosidase or luciferase). Depending on the method used for detection the amount and measurement of the change can vary. Determination of statistical significance is within the ability of those skilled in the art, e.g., the number of standard deviations from the mean that constitute a positive result.

As used herein, "detecting", "detection" and the like are understood that an assay performed for identification of a specific analyte in a sample, e.g., an antigen in a sample or the level of an antigen in a sample. The amount of analyte or activity detected in the sample can be none or below the level of detection of the assay or method.

By "diagnosing" and the like as used herein refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. A diagnostic methods provide an indicator that a disease is or is not present. A single diagnostic test typically does not provide a definitive conclusion regarding the disease state of the subject being tested.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "polynucleotide" or "nucleic acid" as used herein designates mRNA, RNA, cRNA, cDNA or DNA. As used herein, a "nucleic acid encoding a polypeptide" is understood as any possible nucleic acid that upon (transcription and) translation would result in a polypeptide of the desired sequence. The degeneracy of the nucleic acid code is well understood. Further, it is well known that various organisms have preferred codon usage, etc. Determination of a nucleic acid sequence to encode any polypeptide is well within the ability of those of skill in the art.

As used herein, "immunoassay" is understood as any antibody base detection method including, but not limited to enzyme linked immunosorbent assay (ELISA), radioimmune assay (RIA), western blot, immunohistochemistry, immunoprecipitation assay such as Luciferase Immunoprecipitation System (LIPS see, e.g., US Patent Publication 2007/0259336 which is incorporated herein by reference). In a preferred embodiment, the immunoassay is a quantitative.

Antibodies for use in immunoassays include any monoclonal or polyclonal antibody appropriate for use in the specific immunoassay.

By "inhibitory nucleic acid molecule" is meant a polynucleotide that disrupts the expression of a target nucleic acid molecule or an encoded polypeptide. Exemplary inhibitory nucleic acid molecules include, but are not limited to, shRNAs, siRNAs, antisense nucleic acid molecules, and analogs thereof.

As used herein, "isolated" or "purified" when used in reference to a polypeptide means that a naturally polypeptide or protein has been removed from its normal physiological environment (e.g., protein isolated from plasma or tissue, optionally bound to another protein) or is synthesized in a non-natural environment (e.g., artificially synthesized in an in vitro translation system or using chemical synthesis). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. An isolated virus or viral vector is a virus that is removed from the cells, typically in culture, in which the virus was produced.

As used herein, "kits" are understood to contain at least one non-standard laboratory reagent for use in the methods of the invention in appropriate packaging, optionally containing instructions for use. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100.mu.g/ml denatured salmon sperm DNA (ssDNA). In a most preferred embodiment, hybridization will occur at 42° C. C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42.degree. C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Obtaining" is understood herein as manufacturing, purchasing, or otherwise coming into possession of.

As used herein, "operably linked" is understood as joined, preferably by a covalent linkage, e.g., joining an amino-terminus of one peptide, e.g., expressing an enzyme, to a carboxy terminus of another peptide, e.g., expressing a signal sequence to target the protein to a specific cellular compartment; joining a promoter sequence with a protein coding sequence, in a manner that the two or more components that are operably linked either retain their original activity, or gain an activity upon joining such that the activity of the operably linked portions can be assayed and have detectable activity, e.g., enzymatic activity, protein expression activity.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intracardiac, intraperotineal, intrathecal, intracranial, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments). Optionally the peptide further includes one or more modifications such as modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins, Structure and Molecular Properties, 2nd ed., T. E. Creighton, W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-646 (1990); Rattan et al., Ann. N.Y. Acad. Sci. 663:48-62 (1992)).

The term "reduce" or "increase" is meant to alter negatively or positively, respectively, by at least 5%. An alteration may be by 5%, 10%, 25%, 30%, 50%, 75%, or even by 100%.

As used herein, a "reporter protein" or a "reporter polypeptide" is understood as a polypeptide that can be readily detected, preferably quantitatively detected, either directly or indirectly. A reporter polypeptide typically has an enzymatic activity, luciferase activity, alkaline phosphatase activity, beta-galactosidase activity, acetyl transferase activity, etc. wherein catalysis of a reaction with the substrate by the enzyme results in the production of a product, e.g., light, a product that can be detected at a specific wavelength of light, radioactivity, such that the amount of the reporter peptide can be determined in the sample, either as a relative amount, or as an absolute amount by comparison to control samples.

A "sample" as used herein refers to a biological material that is isolated from its environment (e.g., blood or tissue from an animal, cells, or conditioned media from tissue culture) and is suspected of containing, or known to contain an analyte, such as a protein. A sample can also be a partially purified fraction of a tissue or bodily fluid. A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

"Sensitivity and specificity" are statistical measures of the performance of a binary classification test. The sensitivity (also called recall rate in some fields) measures the proportion of actual positives which are correctly identified as such (e.g. the percentage of sick people who are identified as having the condition); and the specificity measures the proportion of negatives which are correctly identified (e.g. the percentage of well people who are identified as not having the condition). They are closely related to the concepts of type I and type II errors. A theoretical, optimal prediction can achieve 100% sensitivity (i.e. predict all people from the sick group as sick) and 100% specificity (i.e. not predict anyone from the healthy group as sick).

The concepts are expressed mathematically as follows:

sensitivity=# true positives/# true positives+# false negatives specificity=# true negatives/# true negatives+# false positives.

By "selectively" is meant the ability to affect the activity or expression of a target molecule without affecting the activity or expression of a non-target molecule. For example, a Cthrc1 inhibitory nucleic acid molecule selectively reduces the levels of Cthrc1 without directly targeting collagen.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

A "subject" as used herein refers to an organism. In certain embodiments, the organism is an animal. In certain embodiments, the subject is a living organism. In certain embodiments, the subject is a cadaver organism. In certain preferred embodiments, the subject is a mammal, including, but not limited to, a human or non-human mammal. In certain embodiments, the subject is a domesticated mammal or a primate including a non-human primate. Examples of subjects include humans, monkeys, dogs, cats, mice, rats, cows, horses, goats, and sheep. A human subject may also be referred to as a patient.

A "subject sample" can be a sample obtained from any subject, typically a blood or serum sample, however the method contemplates the use of any body fluid or tissue from a subject. The sample may be obtained, for example, for diagnosis of a specific individual for the presence or absence of a particular disease or condition.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with diminished cardiac function is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range. This includes all individual sequences when a range of SEQ ID NOs: is provided. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

The invention features compositions and methods that are useful for the treatment or prevention of coronary heart disease, peripheral vascular disease, and stroke featuring compositions that inhibit the expression or activity of Collagen Triple Helix Repeat Containing-1 (Cthrc1). In particular embodiments, the invention features compositions and methods that are useful for the treatment of coronary heart disease, peripheral vascular disease, and/or stroke by interfering with the expression or activity of Cthrc1. The invention is based, at least in part, on the discovery that interfering with the expression of Cthrc1, is useful for outward remodeling of blood vessels. As reported in more detail below, inhibiting the expression of Cthrc1, increased vascularization and perfusion in mouse models of vascular remodeling and ischemia. Following occlusion of left carotid artery in a mouse model of vascular remodeling, increased lumen diameter and blood flow were observed in Cthrc1 deficient mice. In studies assessing recovery from hindlimb ischemia extensive collateral formation (arteriogenesis) and complete recovery from muscle ischemia and edema was observed in Crthrc1 deficient mice. Accordingly, treatment with an agent that reduces the expression or biological activity of Cthrc1 is useful for increasing vascularization and arteriogenesis and reducing ischemia and edema.

Accordingly, the invention provides methods of treating coronary heart disease, peripheral vascular disease, and/or stroke, or disorders or symptoms thereof which comprise administering a therapeutically effective amount of a pharmaceutical composition comprising a compound (e.g., an inhibitory nucleic acid molecule that disrupts Cthrc1 expression) described herein to a subject (e.g., a mammal such as a human). Thus, in one embodiment, the invention provides a method of treating a subject suffering from or susceptible to coronary heart disease, peripheral vascular disease, and/or stroke or disorder or symptom thereof. The method includes the step of administering to the mammal a therapeutic amount of a compound described herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, family history, and the like). The compounds herein may be also used in the treatment of any other disorders in which the expression of Cthrc1 or increased expression of Cthrc1 may be implicated.

Collagen Triple Helix Repeat Containing-1 (Cthrc1) Protein

Collagen triple helix repeat containing-1 (Cthrc1) is a protein having a signal peptide which was isolated from a cDNA library of injured arteries[1]. Cthrc1 has been reported to function as an inhibitor of TGF-β signaling[2]. Cthrc1 is susceptible to cleavage by proteases and purified Cthrc1 forms aggregates, making it difficult to perform cell binding studies and protein interaction studies[3]. Expression analyses of Cthrc1 in tissues have been performed by in situ hybridization, immunohistochemistry and RT-PCR analysis. As described herein, Cthrc1 has also been found in plasma. Cthrc1 plasma levels in healthy human volunteers ranged from 16-440 ng/ml, although the reason for the variation in Cthrc1 plasma levels and its significance is being investigated.

A recent study found no phenotypic abnormalities in Cthrc1 deficient mice and, based largely on in vitro data, a role for Cthrc1 in the planar cell polarity pathway of non-canonical Wnt signaling was reported[4]. A separate mutant Cthrc1 mouse with deletion of exon 2 was reported to have a reduction in bone mass in the adult[5].

Cthrc1$^{tm1Vli}$ null mice (having a Cthrc1 allele generated by deletion of exons 2-4) develop a progressive decline in cardiac function, detectable after 5 weeks of age. However, in most cases this does not lead to symptoms. In more severe cases seen in older mice, this phenotype is characterized by dilation, decreasing contractile performance, and focal fibrotic degeneration of the myocardium. In contrast, in some transgenic mice overexpressing Cthrc1 global cardiac hypertrophy was observed.

Endogenous Cthrc1 protein was detectable in the left atrium of the heart in newborn mice. The cardiovascular system undergoes extensive remodeling after birth. When the ductus arteriosus and the formamen ovale close after birth, the left atrium experiences a dramatic increase in blood volume that needs to be pumped into the left ventricle. The expression of Cthrc1 in the left atrium coincided with this remodeling event.

Isolated, isovolumic perfused mouse heart responded to exogenous Cthrc1 added to the perfusion flow with a sustained increase in cardiac work (20±0.2%) and contractility (19±3.1%) as well as faster relaxation (23±1%). In addition, Cthrc1 caused a significant increase in coronary blood flow of approximately 24%. Without being bound to a particular theory, these findings indicate that Cthrc1 has positive inotropic activity mediated by ionotropic effects, consistent with hormone-like activities of Cthrc1. These effects appear to be independent from the blood flow increasing effects of Cthrc1 in the heart. As described herein, Cthrc1 plays a role in cardiac adaptation to increased demands for cardiac performance. Conditions that impose increased stress on the myocardium, (e.g., hypertension, loss of functional myocardium due to heart disease, heart valve disease, exercise induced hypertrophy) exacerbate a deficiency in Cthrc1, as such symptoms are not observed in all mice lacking Cthrc1.

Without being bound to a particular theory, the reduction of iNOS and eNOS levels seen in the presence of increased Cthrc1 suggests that Cthrc1 functions are mediated by a reduction in nitric oxide production. Because Cthrc1 is expressed in pericytes of postcapillary venules, the dilation of downstream veins in Cthrc1 deficient mice is consistent with the absence of an endogenous NOS inhibitor. Endogenous Cthrc1 is preferentially expressed in remodeling blood vessels, which are not typically found in normal adult mice, and similar NOS levels were observed in wild-type and Cthrc1 deficient mice. Microvascular endothelial cells in vitro responded to Cthrc1 with a reduction in eNOS levels. However, large vessel endothelial cells in vitro did not respond to Cthrc1 with a reduction in eNOS levels. This result suggests preferential effects of Cthrc1 on small vessel endothelium. A reduction of iNOS levels by Cthrc1 was seen in vascular smooth muscle and endogenous Cthrc1 expression occurring in outer mural cells of larger remodeling vessels. Without being bound to a particular theory, Cthrc1 inhibits nitric oxide production in adjacent smooth muscle cells, which in turn explains increased outward remodeling and accelerated collateral formation seen in Cthrc1 deficient mice.

Blood Vessel Formation and Remodeling

Blood vessel formation is a dynamic process that includes one or more steps of blood vessel development and/or maturation, such as angiogenesis, arteriogenesis, vasculogenesis, formation of an immature blood vessel network, blood vessel remodeling, blood vessel stabilization, blood vessel maturation, blood vessel differentiation, or establishment of a functional blood vessel network. Angiogenesis, which involves the growth or sprouting of new microvessels from pre-existing vasculature, and vasculogenesis, which involves de novo vascular growth, is essential to many physiological and pathological conditions, including embryogenesis, cancer, rheumatoid arthritis, diabetic retinopathy, obesity, atherosclerosis, ischemic heart and limb disease, and wound healing. Over 70 diseases have been identified as angiogenesis dependent (Carmeliet, *Nature*, 438:932-6, 2005). Under physiological conditions, the growth of new microvessels is tightly regulated and orchestrated by maintaining a balance between endogenous pro- and anti-angiogenic factors. Tipping the balance of this regulation may lead to either excessive neovascularization, as in cancer, age-related macular degeneration, and rheumatoid arthritis, or insufficient vascularization, as in ischemic heart and limb disease, ischemic brain, and neural degeneration.

Angiogenesis is a complex multistep process that involves interactions between endothelial cells (EC), pericytes, vascular smooth muscle cells, and stromal cells (e.g., stem cells and parenchymal cells). These interactions occur through secreted factors, such as vascular endothelial growth factor (VEGF), platelet-derived growth factor (PDGF), basic fibroblast growth factor (bFGF or FGF-2) and angiopoietins, as well as through cell-cell and cell-extracellular matrix (ECM) interactions. Endothelial cell-ECM interactions regulate numerous processes that are critical for angiogenesis, including endothelial cell migration, proliferation, differentiation and apoptosis. Angiogenic processes include network stabilization and remodeling that may involve the recruitment of stromal cells, as well as the pruning of some vessels. In many cases, angiogenesis occurs as a response to hypoxia. A transcription factor called hypoxia-inducible factor, HIF1α, has been demonstrated to act as an oxygen sensor whose activity leads to upregulation of VEGF in parenchymal and stromal cells (Semenza, *Physiology (Bethesda)*, 19:176-82, 2004). VEGF is secreted as a homodimer in the form of several heparin-binding and non-heparin-binding splice-variant isoforms; it diffuses through the interstitial space and can bind to the endothelial cell receptors VEGFR1 and VEGFR2, as well as co-receptors such as Neuropilin-1, thus initiating a signal transduction cascade that leads to endothelial cell proliferation and migration. The production of endothelial cell matrix metalloproteinases, MMPs, increases as a result of endothelial cell activation; MMPs are necessary for selectively clipping the capillary basement membrane and the ECM, which constitute physical barriers to endothelial cell migration and capillary sprouting. MMPs and their associated molecules also play a crucial role in uncovering cryptic sites of the ECM proteins, a number of which have been identified as anti-angiogenic (Davis et al., *Anat Rec*, 268:252-75, 2002; Folkman, *Annu Rev Med*, 57:1-18, 2006; Rundhaug, *J Cell Mol Med*, 9:267-85, 2005; Schenk and Quaranta, *Trends Cell Biol*, 13:366-75, 2003), and in processing cell-surface receptors (Mott and Werb, *Curr Opin Cell Biol*, 16:558-64, 2004). Vasculogenesis is the development of new blood vessels originating from stem cells, angioblasts, or other precursor cells, such as endothelial progenitor cells (EPCs). These stem cells can be recruited from bone marrow endogenously or implanted therapeutically.

Blood vessel remodeling is the dynamic process of blood vessel enlargement in shape and size which maintains the lumen and maintains blood flow. Arteriogenesis is meant an increase in the diameter of existing arterial vessels.

As described herein, agents that increase angiogenesis and/or arteriogenesis are useful for the treatment of coronary heart disease, peripheral vascular disease, and/or stroke.

Angiogenesis Assays

The biological activity of therapeutic agents of the invention is characterized using any method for assaying angiogenic activity known in the art. nAngiogenesis can be assayed by measuring the number of non-branching blood vessel segments (number of segments per unit area), the functional vascular density (total length of perfused blood vessel per unit area), the vessel diameter, or the vessel volume density (total of calculated blood vessel volume based on length and diameter of each segment per unit area). Methods for measuring angiogenesis are standard, and are described, for example, in Jain et al. (Nat. Rev. Cancer 2: 266-276, 2002).

In vitro angiogenesis assays have been described in detail in recent reviews (Akhtar et al., *Angiogenesis*, 5:75-80, 2002; Auerbach et al., *Cancer Metastasis Rev*, 19:167-72, 2000; Auerbach et al., *Clin Chem*, 49:32-40, 2003; Staton et al., *Int J Exp Pathol*, 85:233-48, 2004; Vailhe et al., *Lab Invest*, 81:439-52, 2001). There are a number of different endothelial cell lineages that have been used in angiogenesis assays: bovine aortic, bovine retinal, rat and mouse microvascular, human aortic, human bladder microvascular, human cardiac microvascular, human dermal microvascular, human lung microvascular and human umbilical vein endothelial cells. All of these endothelial cells are capable of differentiating in vitro and forming capillary-like structures. This process occurs when the cells are cultured in a monolayer of extracellular matrix components, such as the Matrigel (extracellular matrix material similar to basement membrane), type I collagen, fibronectin or laminin. An endothelial cell lineage that is commonly used for testing the angiogenic response is the human umbilical vein endothelial cells (HUVECs).

Cell Proliferation Assay

In these assays angiogenic agents are tested for their ability to increase endothelial cell proliferation or decrease endothelial cell death. An increase in endothelial cell proliferation or decreases endothelial cell death identifies an agent that enhances angiogenesis. The viability and metabolic activity of the cells is measured in the presence of the angiogenic peptides at different concentrations and various time steps. Proliferation assays include WST-1, XTT, Trypan Blue, Alamar Blue and BrdU. In contrast to the MTT assay, in the WST-1 assay the formazan crystals do not need to be solubilized by the addition of a detergent; they are soluble to the cell medium.

Preferably, an agent of the invention increases cell proliferation by at least about 5%, 10%, 20% or 25%. More preferably, cell proliferation is increased by at least 50%, 75%, or even by 100%.

Polynucleotide Therapy

If desired, nucleic acid molecules that encode therapeutic polypeptides are delivered to stem cells, such as endothelial stem cells, bone marrow-derived stem cells, hematopoietic stem cells, their precursors, or progenitors. In other approaches, nucleic acid molecules are delivered to cells of a tissue (e.g., pancreatic tissue, liver tissue, heart tissue, etc.). The nucleic acid molecules must be delivered to the cells of a subject in a form in which they can be taken up so that therapeutically effective levels of the therapeutic polypeptide (e.g., stem cell recruiting factor, such as SDF-1; a hepatocyte growth factor; a cardiocyte growth factor; etc.) or fragment thereof can be produced.

A variety of expression systems exists for the production of therapeutic polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (e.g., pET-28) (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3× may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag (SEQ ID NO: 17), that binds to nickel column.

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

If desired, a vector expressing stem cell recruiting factors is administered to a tissue or organ. SDF-1 (also called PBSF) (Campbell et al. (1998) *Science* 279(5349):381-4), 6-C-kine (also called Exodus-2), and MIP-3β (also called ELC or Exodus-3) induced adhesion of most circulating lymphocytes, including most $CD4^+$ T cells; and MIP-3α (also called LARC or Exodus-1) triggered adhesion of memory, but not naive, $CD4^+$ T cells. Tangemann et al. (1998) *J. Immunol.* 161:6330-7 disclose the role of secondary lymphoid-tissue chemokine (SLC), a high endothelial venule (HEV)-associated chemokine, with the homing of lymphocytes to secondary lymphoid organs. Campbell et al. (1998) *J. Cell Biol* 141(4):1053-9 describe the receptor for SLC as CCR7, and that its ligand, SLC, can trigger rapid integrin-dependent arrest of lymphocytes rolling under physiological shear.

In still other approaches, a vector encoding a polypeptide characteristically expressed in a cell of interest is introduced to a stem cell of the invention.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a stem cell recruiting factor, variant, or a fragment thereof, can be cloned into a retroviral vector and expression can be driven from its endogenous promoter, from the retroviral long terminal repeat, or from a promoter specific for a tissue or cell of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer a therapeutic polynucleotide in pancreas, liver, heart, or another tissue or organ of interest.

Non-viral approaches can also be employed for the introduction of a therapeutic to a cell of a subject (e.g., a cell or tissue). For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann et al., *Proc. Natl. Acad. Sci. USA* 88:4626-4630 (1991)), adenosine deaminase, phosphoglycerol kinase (PGK), pyruvate kinase, phosphoglycerol mutase, the actin promoter (Lai et al., *Proc. Natl. Acad. Sci. USA* 86: 10006-10010 (1989)), and other constitutive promoters known to those of skill in the art. In addition, many viral promoters function constitutively in eukaryotic cells. These include: the early and late promoters of SV40; the long terminal repeats (LTR) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified stem cell and/or in a cell of the tissue having a deficiency in cell number. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the subject.

In addition to at least one promoter and at least one heterologous nucleic acid encoding the therapeutic agent, the expression vector preferably includes a selection gene, for example, a neomycin resistance gene, for facilitating selection of stem cells that have been transfected or transduced with the expression vector.

If desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a recombinant stem cell recruiting factor, variant, or fragment thereof, either directly to the site of a potential or actual disease-affected tissue or systemically (for example, by any conventional recombinant protein administration technique). The dosage of the administered protein depends on a number of factors, including the size and health of the individual subject. For any particular subject, the specific dosage regimes should be adjusted over time according to the individual need and the professional judgment of the person administering or supervising the administration of the compositions.

Non-Peptide Agents

The invention also provides small organic molecules, such as those natural products, or those compounds synthesized by conventional organic synthesis or combinatorial organic synthesis that selectively bind to Cthrc1 and thereby inhibit the binding of an inflammatory cell. Compounds can be tested for their ability to bind to a Cthrc1, for example, by using a column binding technique.

Other suitable non-peptidic compounds include, for example, oligonucleotides. Oligonucleotides as used herein refers to any heteropolymeric material containing purine, pyrimidine and other aromatic bases. DNA and RNA oligonucleotides are suitable for use with the invention, as are oligonucleotides with sugar (e.g., 2' alkylated riboses) and backbone modifications (e.g., phosphorothioate oligonucleotides). Oligonucleotides may present commonly found purine and pyrimidine bases such as adenine, thymine, guanine, cytidine and uridine, as well as bases modified within the heterocyclic ring portion (e.g., 7-deazaguanine) or in exocyclic positions. Oligonucleotide also encompasses heteropolymers with distinct structures that also present aromatic bases, including polyamide nucleic acids and the like.

An oligonucleotide antagonist of the invention can be generated by a number of methods known to one of skill in the art. In one embodiment, a pool of oligonucleotides is generated containing a large number of sequences. Pools can be generated, for example, by solid phase synthesis using mixtures of monomers at an elongation step. The pool of oligonucleotides is sorted by passing a solution-containing the pool over a solid matrix to which a Cthrc1 or fragment thereof has been affixed. Sequences within the pool that bind to the Cthrc1 are retained on the solid matrix. These sequences are eluted with a solution of different salt concentration or pH. Sequences selected are subjected to a second selection step. The selected pool is passed over a second solid matrix to which native collagen has been affixed. The column retains those sequences that bind to the native collagen, thus, enriching the pool for sequences specific for the Cthrc1. The pool can be amplified and, if necessary, mutagenized and the process repeated until the pool shows the characterstics of an antagonist of the invention. Individual antagonists can be identified by sequencing members of the oligonucleotide pool, usually after cloning said sequences into a host organism such as E. coli.

Cthrc1 can also be used as an agent in screening methods to identify compounds that bind to the same receptors or target proteins as Cthrc1. Such agents could provide small molecules or other compounds that can increase cardiac output without increasing heart rate as Cthrc1. Such screening methods are well known in the art, and one such method is exemplified below in the Examples.

Inhibitory Nucleic Acids

Inhibitory nucleic acid molecules are those oligonucleotides that selectively inhibit the expression or activity of a Cthrc1 polypeptide or nucleic acid molecule. Such oligonucleotides include single and double stranded nucleic acid molecules (e.g., DNA, RNA, and analogs thereof) that are complementary to or that bind a nucleic acid molecule that encodes a Cthrc1 receptor polypeptide (e.g., antisense molecules, RNAi, siRNA, shRNA) as well as nucleic acid molecules that bind directly to a Cthrc1 polypeptide to modulate its biological activity (e.g., aptamers).

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an siRNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of a p55 or p75 TNF-α receptor polypeptide gene can be used to design small interfering RNAs (siRNAs). The 21 to 25 nucleotide siRNAs may be used, for example, as therapeutics to treat a neoplastic disease or disorder.

The inhibitory nucleic acid molecules of the present invention may be employed as double-stranded RNAs for RNA interference (RNAi)-mediated knock-down of p55 or p75 TNF-α receptor polypeptide expression. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

Ribozymes

Catalytic RNA molecules or ribozymes that include an antisense Cthrc1 sequence of the present invention can be used to inhibit expression of Cthrc1 nucleic acid molecule or polypeptide in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

shRNA

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). In one embodiment of the invention, the shRNA molecule is made that includes between eight and twenty-one consecutive nucleobases of a Cthrc1 gene. For expression of shRNAs within cells, plasmid vectors containing either the polymerase III H1-RNA or U6 promoter, a cloning site for the stem-looped RNA insert, and a 4-5-thymidine transcription termination signal can be employed (e.g., pGeneClip Neomycin Vector; Promega Corporation). The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs.

For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Oligonucleotides and Other Nucleobase Oligomers

At least two types of oligonucleotides induce the cleavage of RNA by RNase H: polydeoxynucleotides with phosphodiester (PO) or phosphorothioate (PS) linkages. Although 2'-OMe-RNA sequences exhibit a high affinity for RNA targets, these sequences are not substrates for RNase H. A desirable oligonucleotide is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed, including covalently-closed multiple antisense (CMAS) oligonucleotides (Moon et al., Biochem J. 346:295-303, 2000; PCT Publication No. WO 00/61595), ribbon-type antisense (RiAS) oligonucleotides (Moon et al., J. Biol. Chem. 275: 4647-4653, 2000; PCT Publication No. WO 00/61595), and large circular antisense oligonucleotides (U.S. Patent Application Publication No. US 2002/0168631 A1).

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3' to 5' phosphodiester linkage.

Specific examples of preferred nucleobase oligomers useful in this invention include oligonucleotides containing modified backbones or non-natural internucleoside linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriest-ers, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. The nucleobase units are maintained for hybridization with a nucleic acid molecule encoding a p75/TNF-α receptor or p55/TNF-α receptor. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N ($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)nON[($CH_2$)$_n$$CH_3$)]$_2$, where n and m are from 1 to about 10. Other preferred nucleobase oligomers include one of the following at the 2' position: $C_1$ to $C_{10}$ lower alkyl, substituted lower alkyl, alkaryl, aralkyl, O-alkaryl, or O-aralkyl, SH, S$CH_3$, OCN, Cl, Br, CN, $CF_3$, O$CF_3$, SO$CH_3$, $SO_2CH_3$, O$NO_2$, $NO_2$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O- methyl and 2'-methoxyethoxy (2'-O—CH$_2$CH$_2$OCH$_3$, also known as 2'-O-(2-methoxyethyl) or 2'-MOE). Another desirable modification is 2'-dimethylaminooxyethoxy (i.e., O(CH$_2$)$_2$ON(CH$_3$)$_2$), also known as 2'-DMAOE. Other modifications include, 2'-aminopropoxy (2'-OCH$_2$CH$_2$CH$_2$NH$_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-5-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241; 5,391,723; 5,414,077; 5,416,203; 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The nucleobase oligomers used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Delivery of Nucleobase Oligomers

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Antibodies

In certain preferred embodiments, the present invention provides Cthrc1 antagonists in the form of antibodies. Antibody antagonists as described by the present invention can be used to alter the activity of one or more types of inflammatory cells in a subject. Antibody antagonists as described by the present invention can be used to treat or prevent fibrosis or inflammation.

Antibodies are well known to those of ordinary skill in the science of immunology. As used herein, the term "antibodies" includes polyclonal antibodies, affinity-purified polyclonal antibodies, monoclonal antibodies, and antigen-binding fragments, such as F(ab')2 and Fab proteolytic fragments. Genetically engineered intact antibodies or fragments, such as chimeric antibodies, Fv fragments, single chain antibodies, and the like, as well as synthetic antigen-binding peptides and polypeptides, are also included. Non-human antibodies may be humanized by grafting non-human CDRs onto human framework and constant regions, or by incorporating the entire non-human variable domains. In certain preferred embodiments, humanized antibodies may retain non-human residues within the human variable region framework domains to enhance proper binding characteristics. Through humanizing antibodies, biological half-life may be increased, and the potential for adverse immune reactions upon administration to humans is reduced. Monoclonal antibodies can also be produced in mice that have been genetically altered to produce antibodies that have a human structure.

"Antibody" means not only intact antibody molecules, but also fragments of antibody molecules that retain immunogen binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., J. Nucl. Med. 24:316-325 (1983).

Examples of antibodies include monoclonal antibodies, polyclonal antibodies, the preparation and use of which are known to the skilled artisan. Other exemplary antibodies include whole native antibodies, bispecific antibodies, Fab, Fab', single chain V region fragments (scFv) and fusion polypeptides. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

The phrase "monoclonal antibody" refers to a population of antibody molecules that contain only one species of antibody combining site capable of immunoreacting with a particular epitope. A monoclonal antibody may therefore contain an antibody molecule having a plurality of antibody combining sites, each immunospecific for a different epitope, e.g., a bispecific monoclonal antibody.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes. Antibodies can be made by any of the methods known in the art, where the target is Cthrc1.

An "epitope" is a region of a protein to which an antibody can bind. See, for example, Geysen et al., Proc. Natl. Acad. Sci. USA 81:3998-4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., Science 219:660-666, 1983. Immunogenic, epitope-bearing polypeptides contain a sequence of at least six, often at least nine, more often from 15 to about 30 contiguous amino acid residues of Cthrc1. In certain embodiments, an agent of the invention specifically binds to an epitope of Cthrc1.

One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a Cthrc1 epitope as described herein, or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a Cthrc1 epitope as described herein, or immunogenic fragments thereof, can be expressed in cells in vitro, followed by isolation of the receptor and administration of the receptor to a suitable host in which antibodies are raised.

Using either approach, antibodies can then be purified from the host. Antibody purification methods may include salt precipitation (for example, with ammonium sulfate), ion exchange chromatography (for example, on a cationic or anionic exchange column, preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition, e.g., Pristane.

Monoclonal antibodies (Mabs) can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

In particular embodiments of the invention, an antibody is used to detect a Cthrc1 epitope. The antibody can be prepared against any Cthrc1 epitope using techniques discussed and known to one of ordinary skill in the art. In one example, to detect a collagen cryptic epitope, the antibody can be prepared against the sequence GDASTGWNSVSRIIIEELP (SEQ ID NO: 1) or VVDLYNGMCLQGPAGV (SEQ ID NO: 2).

In certain cases, the immunogenicity of a polypeptide immunogen may be increased through the use of an adjuvant.

Alternative techniques for generating or selecting antibodies include in vitro exposure of lymphocytes to a polypeptide immunogen, and selection of antibody display libraries in phage or similar vectors (for instance, through use of immobilized or labeled polypeptide). Techniques for creating and screening such random peptide display libraries are known in the art (e.g., Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698), and random peptide display libraries and kits for screening such libraries are available commercially, for instance from Clontech Laboratories (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the epitope sequences disclosed herein to identify proteins that bind to preferred epitopes.

Antibodies are determined to be specifically binding if they bind to their intended target (e.g., Cthrc1 types I, II, III, IV) with a greater affinity than the binding affinity to control (e.g., non-Cthrc1 type-IV) polypeptide or protein. The binding affinity of an antibody can be readily determined by one of ordinary skill in the art, for example, by Scatchard analysis (Scatchard, G., Ann NY Acad. Sci. 51: 660-672, 1949). Methods for screening and isolating specific antibodies are well known in the art. See, for example, Paul (ed.), Fundamental Immunology, Raven Press, 1993; Getzoff et al., Adv. in Immunol. 43:1-98, 1988; Goding (ed.), Monoclonal Antibodies: Principles and Practice, Academic Press Ltd., 1996; and Benjamin et al., Ann. Rev. Immunol. 2:67-101, 1984.

A variety of assays known to those skilled in the art can be utilized to detect antibodies that specifically bind to Cthrc1. Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assays, inhibition or competition assays, and sandwich assays.

Pharmaceutical Compositions and Administration

The present invention contemplates pharmaceutical preparations comprising an agent that binds to Cthrc1 together with a pharmaceutically acceptable carrier. Polypeptides of the invention may be administered as part of a pharmaceutical composition. The compositions should be sterile and contain a therapeutically effective amount of the polypeptides in a unit of weight or volume suitable for administration to a subject.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethyl amine, 2-ethylamino ethanol, histidine, procaine and the like. Particularly preferred are the salts of TFA and HCl.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an inflammation inhibiting amount or a fibrosis inhibiting amount of an Cthrc1 antagonist of the present invention, typically formulated to contain an amount of at least 0.1 weight percent of antagonist per weight of total therapeutic composition. A weight percent is a ratio by weight of inhibitor to total composition. Thus, for example, 0.1 weight percent is 0.1 grams of inhibitor per 100 grams of total composition.

These compositions can be stored in unit or multi-dose containers, for example, sealed ampoules or vials, as an aqueous solution or as a lyophilized formulation for reconstitution. As an example of a lyophilized formulation, 10 mL vials are filled with 5 mL of sterile-filtered 1% (w/v) aqueous antagonist polypeptide solution, and the resulting mixture can then be lyophilized. The infusion solution can be prepared by reconstituting the lyophilized material using sterile Water-for-Injection (WFI).

The compositions can be administered in effective amounts. The effective amount will depend upon the mode of administration, the particular condition being treated, and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

The dosage ranges for the administration of the Cthrc1 antagonist depend upon the form of the antagonist, and its potency, as described further herein, and are amounts large enough to produce the desired effect in which inflammation or fibrosis and the disease symptoms mediated by inflammation or fibrosis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage also can be adjusted by the individual physician in the event of any complication.

A therapeutically effective amount is an amount of Cthrc1 antagonist sufficient to produce a measurable inhibition of inflammation or fibrosis in the tissue being treated. Fibrosis can be measured by various non-invasive methods including palpation, ocular examination, retinal examination, X-ray, ultrasound, MRI, as well as invasive methods such as biopsy with histopathological examination and molecular marker analysis, endoscopy, isotope incorporation and gamma scintigraphy. Inflammation can be measured noninvasively by palpation, ocular examination, retinal examination, assessment of body and tissue temperature, and functional evaluation of blood flow in tissue by ultrasound or MRI as well as invasively by methods such as biopsy with histopathological examination and molecular marker analysis, endoscopy, isotope incorporation and gamma scintigraphy. All above methods of measurement are used in conjunction with assessment of clinical parameters for function of the affected tissue.

A therapeutically effective amount of an agent of this invention in the form of a monoclonal antibody is typically an amount such that when administered in a physiologically tolerable composition is sufficient to achieve a plasma concentration of from about 0.01 microgram (ug) per milliliter (mL) to about 10 ug/mL, preferably from about 1 ug/mL to about 5 ug/mL, and usually about 5 ug/mL. Stated differently, the dosage can vary from about 0.5 mg/kg to about 100 mg/kg, preferably from about 0.5 mg/kg to about 50 mg/kg (e.g., 0.5, 1, 2, 3, 5, 10, 12, 15, 20, 25, 30, 35, 40, 45, 50 mg/kg) in one or more dose administrations daily, for one or several days. In one embodiment, the antibody dose is 0.5, 1, 5, 10, 15, 20, or 25 mg/kg.

Where the agent is in the form of a fragment of a monoclonal antibody, the amount can readily be adjusted based on the mass of the fragment relative to the mass of the whole antibody. A preferred plasma concentration in molarity is from about 2 micromolar (uM) to about 5 millimolar (mM) and preferably about 100 uM to 1 mM antibody antagonist.

A therapeutically effective amount of a Cthrc1 antagonist of this invention in the form of a polypeptide, or small molecule, is typically an amount of polypeptide such that when administered in a physiologically tolerable composition is sufficient to achieve a plasma concentration of from about 0.1 microgram (ug) per milliliter (mL) to about 200 ug/mL, or from about 1 ug/mL to about 150 ug/mL. Based on a polypeptide having a mass of about 500 grams per mole, in one embodiment, the plasma concentration in molarity is from about 2 micromolar (uM) to about 5 millimolar (mM) or from 100 uM to 1 mM polypeptide antagonist. In other embodiments, the doses of small peptides range from about 500 mg/Kg to about 1.0 g/kg (e.g., 500, 600, 700, 750, 800, 900, 1000 mg/kg).

The agents of the invention can be administered parenterally by injection or by gradual infusion over time. In other embodiments, agents are administered intravenously, intraperitoneally, intramuscularly, subcutaneously, intracavity, transdermally, topically, intraocularly, orally, intranasally, and can be delivered by peristaltic means. In one particular embodiment, an agent of the invention is locally delivered to a site of inflammation or fibrosis.

In one embodiment, a therapeutic compositions containing an agent of this invention are administered in a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Cthrc1 can be administered as a peptide, either modified or unmodified, for example to modify the pharmacokinetic and/or pharmacodynamic properties of the peptide. A Cthrc1 peptide can be administered as a full-length peptide, or as a peptide not including the signal sequence (corresponding to amino acids 1 to 30 of the sequence). The peptide can be delivered as any of the peptide fragments taught in U.S. Pat. No. 6,630,325 or any of U.S. patent application Ser. Nos. 09/692,081, 10/045,992, and 10/939,233. Cthrc1 can form a multimer. Cthrc1 can be administered as a dimer, trimer, etc. Methods of expressing proteins such that they form dimeric and trimeric structures (i.e., take on their native conformations) is well known in the art.

The amount and frequency of administration of Cthrc1 would depend on a number of factors including, but not limited to, the condition to be treated. As demonstrated herein, both increasing Cthrc1 expression above normal levels and eliminating Cthrc1 expression has detrimental effects on subjects. For example, in response to an acute condition (e.g., heart attack) a subject could be administered a bolus of Cthrc1. In a subject found to have chronically low levels of Cthrc1, Cthrc1 could be administered to return the subject to a normal level of Cthrc1.

Therapy

As demonstrated herein, both an excess and a deficiency of Cthrc1 can result in a pathological condition. Subjects suffering, suspected of suffering, or prone to pathological cardiac conditions can be tested and monitored for expression levels of Cthrc1. As demonstrated from the small sample herein, the possible serum levels of Cthrc1 vary widely, and appear to vary more widely within groups of men rather than groups of women. Determining Cthrc1 levels can be performed at a single time point, or Cthrc1 levels can be monitored over time, as are many diagnostic markers, and substantial changes in Cthrc1 levels can be an indication that further testing for cardiac function should be performed. Testing can be done using any assay specific for Cthrc1, for example any immunoassay, preferably an assay that is amenable to high throughput and/or automated screening methods. Antibodies to various portions of Cthrc1 can be generated using routine methods. Methods of epitope selection, antigen preparation, and antibody production are well known to those of skill in the art.

Therapy employing a Cthrc1 antagonist (e.g., an agent that inhibits the expression or activity of Cthrc1) is also provided by the invention. Therapy may be provided wherever therapy for coronary heart disease, peripheral vascular disease, or stroke is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

An inhibitory nucleic acid described herein, or other selective inhibitor of Cthrc1, may be administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be topical, parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for Cthrc1 modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. "Therapeutically effective amount" is intended to include an amount of a compound useful in the present invention or an amount of the combination of compounds claimed, e.g., to treat or prevent the disease or disorder, or to treat the symptoms of the disease or disorder, in a host. The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is advantageously demonstrated at suboptimal concentrations of the compounds. Synergy can be in terms of lower cytotoxicity, increased activity, or some other beneficial effect of the combination compared with the individual components. The preferred dosage of an inhibitory nucleic acid of the invention is likely to depend on such variables as the type and extent of the disorder, the overall health status of the particular patient, the formulation of the compound excipients, and its route of administration. If desired, treatment with an agent of the invention may be combined with therapies for the treatment of coronary heart disease, peripheral vascular disease, or stroke.

For any of the methods of application described above, an agent of the invention is desirably administered intravenously or is applied to the site of coronary heart disease, peripheral vascular disease, or stroke (e.g., by injection).

Methods for Evaluating Therapeutic Efficacy

In one approach, the efficacy of the treatment is evaluated by measuring, for example, the biological function of the treated organ (e.g., cardiac cell function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. Preferably, the tissue is cardiac tissue and, preferably, the organ is heart.

Methods for Evaluating Cardiac Function

Compositions of the invention may be used to enhance cardiac function in a subject having reduced cardiac function. Methods for measuring the biological function of the heart (e.g., contractile function) are standard in the art and are described, for example, in the Textbook of Medical Physiology, Tenth edition, (Guyton et al., W.B. Saunders Co., 2000). In the invention, cardiac function is increased by at least 5%, 10%, 15%, 20%, 30%, 40%, 50%, 60%, 70%, 80%, 90%, or even 100% relative to the cardiac function present in a naturally-occurring, corresponding tissue or organ. Most advantageously, cardiac function is enhanced or damage is reversed, such that the function is substantially normal (e.g., 85%, 90%, 95%, or 100% of the cardiac function of a healthy control subject). Reduced cardiac function may result from conditions such as cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy (e.g., hypertrophic cardiomyopathy originating from a genetic or a secondary cause), post ischemic and post-infarction cardiac remodeling and cardiac failure.

Any number of standard methods are available for assaying cardiovascular function. Preferably, cardiovascular function in a subject (e.g., a human) is assessed using non-invasive means, such as measuring net cardiac ejection (ejection fraction, fractional shortening, and ventricular end-systolic volume) by an imaging method such echocardiography, nuclear or radiocontrast ventriculography, or magnetic resonance imaging, and systolic tissue velocity as measured by tissue Doppler imaging. Systolic contractility can also be measured noninvasively using blood pressure measurements combined with assessment of heart outflow (to assess power), or with volumes (to assess peak muscle stiffening). Measures of cardiovascular diastolic function include ventricular compliance, which is typically measured by the simultaneous measurement of pressure and volume, early diastolic left ventricular filling rate and relaxation rate (can be assessed from echoDoppler measurements). Other measures of cardiac function include myocardial contractility, resting stroke volume, resting heart rate, resting cardiac index (cardiac output per unit of time [L/minute], measured while seated and divided by body surface area [m$^2$])) total aerobic capacity, cardiovascular performance during exercise, peak exercise capacity, peak oxygen ($O_2$) consumption, or by any other method known in the art or described herein.

Measures of vascular function include determination of total ventricular afterload, which depends on a number of factors, including peripheral vascular resistance, aortic impedance, arterial compliance, wave reflections, and aortic pulse wave velocity, Methods for assaying cardiovascular function include any one or more of the following: Doppler echocardiography, 2-dimensional echo-Doppler imaging, pulse-wave Doppler, continuous wave Doppler, oscillometric arm cuff, tissue Doppler imaging, cardiac catheterization, magnetic resonance imaging, positron emission tomography, chest X-ray, X ray contrast ventriculography, nuclear imaging ventriculography, computed tomography imaging, rapid spiral computerized tomographic imaging, 3-D echocardiography, invasive cardiac pressures, invasive cardiac flows, invasive cardiac cardiac pressure-volume loops (conductance catheter), non-invasive cardiac pressure-volume loops.

Kits

The invention provides kits for the treatment or prevention of coronary heart disease, peripheral vascular disease, and/or stroke. In one embodiment, the kit includes a therapeutic or prophylactic composition containing an effective amount of an agent described herein, such as an inhibitory nucleic acid to Cthrc1 in unit dosage form. In some embodiments, the kit comprises a sterile container that contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing coronary heart disease, peripheral vascular disease, and/or stroke. The instructions will generally include information about the use of the composition for the treatment or prevention of coronary heart disease, peripheral vascular disease, and/or stroke. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

This invention is further illustrated by the following examples, which should not be construed as limiting. All documents mentioned herein are incorporated herein by reference.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology"

(Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1. Generation of Cthrc1 Deficient Mice and Cthrc1 Overexpressing Mice

To study the consequences of Cthrc1 deficiency in the cardiovascular system, a novel targeted Cthrc1 allele was developed by deletion of exons 2-4 (Cthrc1$^{tm1Vli}$, FIG. 1A). The Cthrc1 null allele replaced exons 2-4 with a neomycin cassette using the targeting vector pKO Scrambler NTKV-1905 (Stratagene). Exon 1 contains a 5' untranslated sequence and the N-terminal 52 amino acids of Cthrc1, including the signal sequence and an additional 20 amino acids, which includes the propeptide[3]. Because the propeptide has not been associated with a function, it was anticipated that the mutant allele would result in a Cthrc1 null phenotype.

Figure 1C:
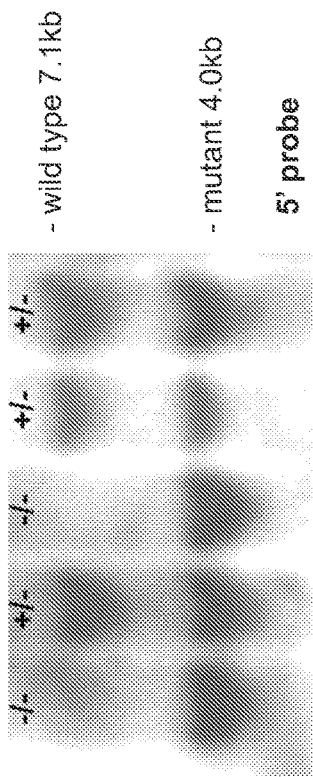
FIG. 1C shows Southern blot analysis of Embryonic fibroblasts: Southern blot analysis of genomic DNA isolated from embryonic fibroblast cultures established from E12.5 mouse embryos of heterozygous Cthrc1 matings.
Figure 1B:
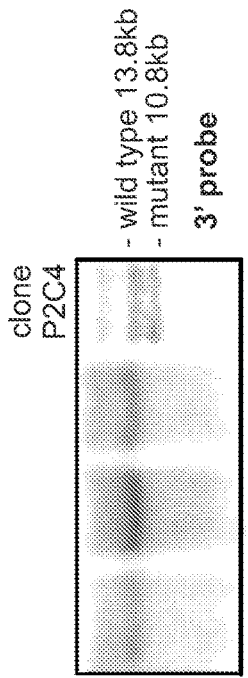

Embryonic stem cell clones were screened by Southern blotting and positive clones injected into blastocysts (FIG. 1B). Two chimeras were obtained and bred with C57BL/6 mice, producing offspring with agouti coat color indicating germ line transmission. Their genotypes were verified by Southern blotting and a PCR screen that amplified the wild-type allele (primers: 5'-CCACTGGAAACCTCTG-GAGTTG-3' (SEQ ID NO: 3) and 5'-AAGTTCACA-CAAAGGAAGCCCCGC-3' (SEQ ID NO: 4)) and the mutant allele (primers: 5"-GTGTGTTTTGAGGTGTG-GTCCC-3' (SEQ ID NO: 5) and 5'TGGATGTGGAATGT-GTGCGAGG-3 (SEQ ID NO: 6)) (FIG. 1C). Mice having the mutant Cthrc1 allele were backcrossed more than 11 generations to obtain mice having a 129SvEv genetic background. The Cthrc1$^{-/-}$ mice revealed no obvious developmental abnormalities.

Figure 2:
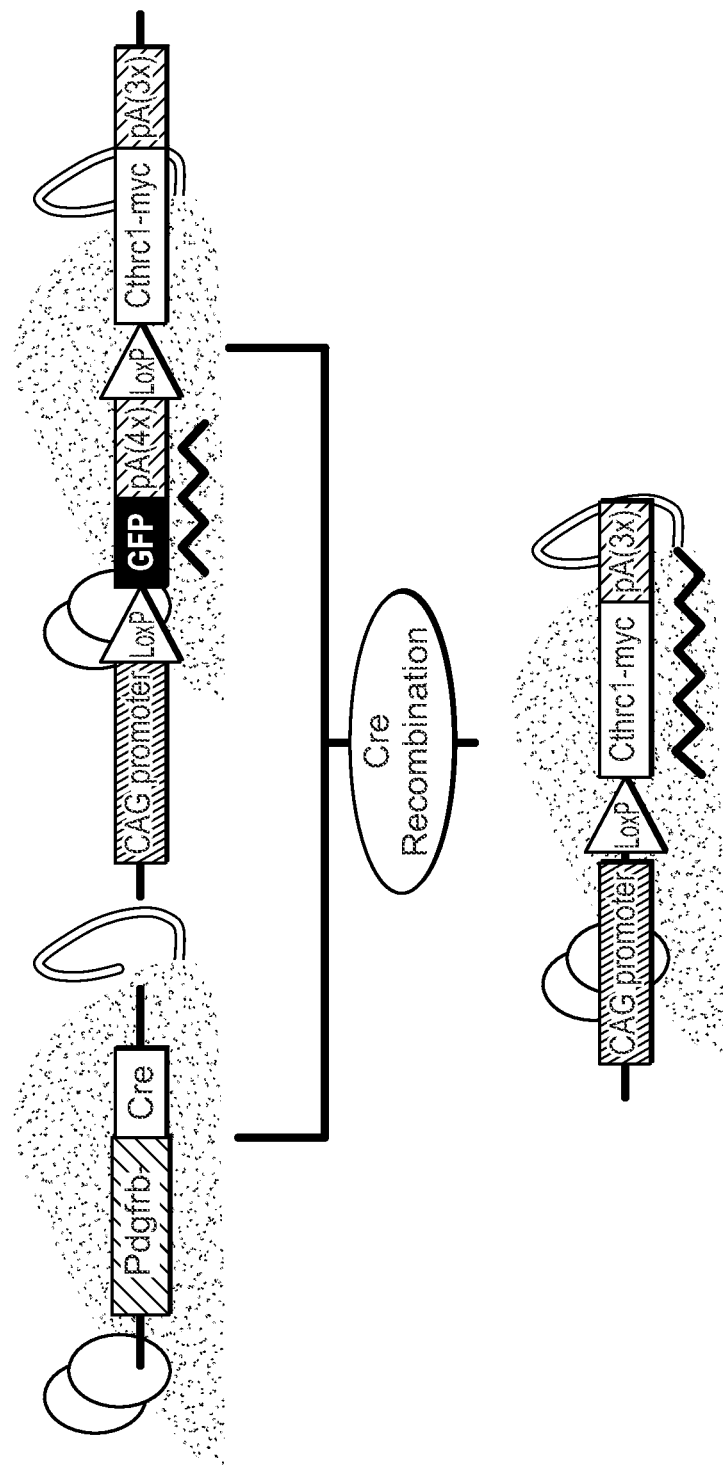
FIG. 2 depicts the generation of transgenic mice expressing Cre-inducible Cthrc1 with a C-terminal myc tag, Tg(CagGfp-Cthrc1myc)$^{11Vli}$. This transgenic mouse line expresses GFP under the control of the CAG promoter in the absence of Cre and upon breeding with Tg(Pdgfrb-Cre)$^{27Vli}$ mice the GFP cassette is removed and the Cthrc1-myc transgene is expressed in cells where the Pdgfrb promoter is active.

Cre-inducible transgenic mice expressing myc-tagged Cthrc1, Tg(CagGfp-Cthrc1myc)[11Vli], were generated and bred with Tg(Pdgfrb-Cre)[27Vli] to obtain double transgenic mice expressing Cthrc1 under the control of the Pdgfrb promoter, which is active in smooth muscle (FIG. 2). In some studies, transgenic mice overexpressing Cthrc1 (under control of the constitutive CMV promoter, (Tg(CMV-Cthrc1myc)[15Vli])[1] were used.

As described herein, it has been discovered that Cthrc1 has a role in the maintenance of cardiac performance. Similar to previously published Cthrc1 deficient mouse mutants, Cthrc1 deficient mice described herein did not display any apparent developmental abnormalities[4,5] and a cardiac phenotype developed postnatally over the course of weeks to months in a small percentage of mice. After back-crossing for more than 11 generations the Cthrc1 deficient mice were on a pure 129SvEv genetic background. In contrast, the mutant described by Kimura et al.[5] was backcrossed onto a C57BL/6 background for 8 generations. The Cthrc1 mutants reported by Yamamoto et al.[4] displayed a phenotype suggestive of altered Wnt signaling via the planar cell polarity pathway only in conjunction with an additional mutation in one of the Vang12 alleles and only on a mixed 129SvEv-057BL/6 background.

The Cthrc1 gene has 4 exons and the present targeting approach involved deletion of exons 2, 3, and 4, which left only exon 1 intact encoding the signal peptide plus an additional 20 amino acids preceding the collagen-like domain. In contrast, the other two published Cthrc1 mutant mice[4,5] were deficient in exon 1 or exon 2. Studies have demonstrated that an N terminal truncation of Cthrc1 upstream of the collagen-like domain does occur, resulting in even greater activity of the molecule[3]. Therefore, the present targeting approach has resulted in the generation of a complete Cthrc1 null allele.

The Cthrc1 deficient mice described herein display a decline in cardiac function over the course of months that in most cases remains asymptomatic (whereas some mice overexpressing Cthrc1 develop cardiac hypertrophy). The decrease in cardiac function in Cthrc1$^{-/-}$ mice developed slowly, and the heart rate measured in 11 week old animals under anesthesia was similar among wild type and Cthrc1 null mice (Table 1). In addition, histological abnormalities with degeneration and fibrosis of the myocardium were typically not seen before the mutant mice were several months of age. These findings indicate that the development of cardiac dysfunction as a result of Cthrc1 deficiency is a chronic process. The data also indicate that Cthrc1 has important functions in maintaining cardiac function. Furthermore, the increase in cardiac performance in response to administered Cthrc1 (6 ng/ml) are suggestive of a receptor mediated effect elicited by the ligand Cthrc1.

The underlying molecular mechanism for the cardiac phenotype still needs to be determined, but it appears to be likely that the mechanism is different from altered PCP Wnt signaling reported by Yamamoto et al[4], whereby Cthrc1 functions extracellularly as part of a Cthrc1-Wnt-Fzd/Ror2 complex. Previous studies had demonstrated a role for Cthrc1 in inhibition of TGF-β signaling in smooth muscle cells, but these studies involved effects of Cthrc1 that occurred many hours to days after stimulation with Cthrc1[3]. The cardiac effects of infused Cthrc1 described here were immediate, suggestive of a different signaling mechanism affecting coronary flow as well as the myocardium.

Figure 5:
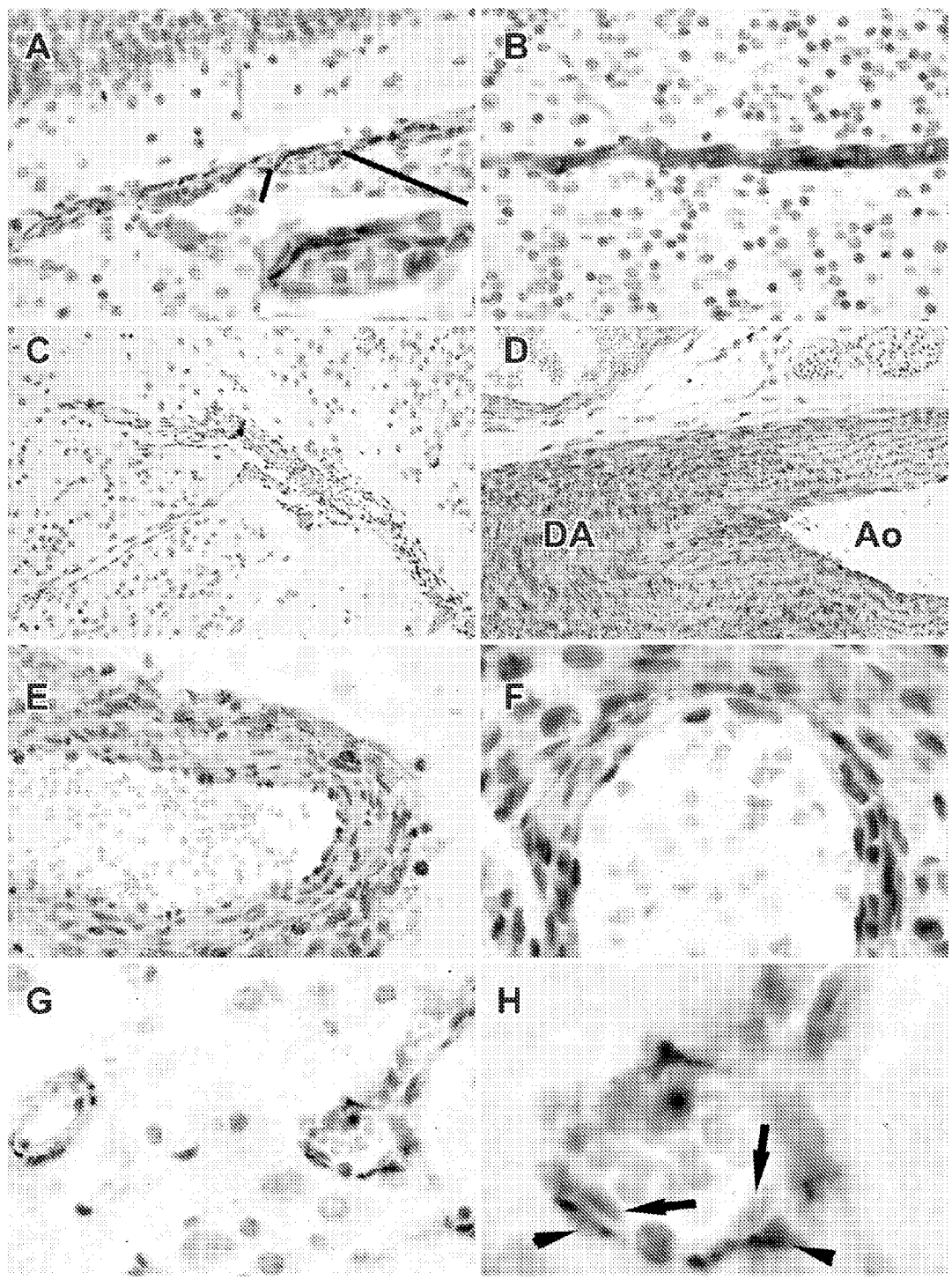
FIGS. 5A-5H depict representative photomicrographs of Cthrc1 immunohistochemistry (in brown) performed on newborn wildtype mice (FIGS. 5A, 5B, 5D, 5E, 5F), a newborn Cthrc1$^{-/-}$ mouse (FIG. 5C), and a mouse germline testicular tumor (FIGS. 5G and 5H).

The results presented herein showing the detection of Cthrc1 in plasma indicate that Cthrc1 functions as a cardiotropic hormone. Cthrc1 is expressed in many tissue samples as detected by RT-PCR, but, without being bound to a particular theory, it is believed Cthrc1 expression in pericytes of postcapillary venules contributes to plasma levels (FIG. 5).

Example 2. Detection of Cthrc1 in Plasma

Without being bound to a particular theory, it is likely that Cthrc1 is a positive ionotrope, consistent with hormone-like activities of Cthrc1. To obtain additional evidence for Cthrc1 as a circulating hormone, an ELISA was developed for detection of Cthrc1 in human plasma. In healthy volunteers Cthrc1 plasma levels ranged from 16-440 ng/ml. An enzyme-linkedin immunosorbent assay (ELISA) was developed to measure Cthrc1 levels in human plasma. Cthrc1 levels in human plasma in healthy male volunteers ranged from 16 ng/ml to 440 ng/ml (FIG. 3). In most samples levels were at the low end of the spectrum close to the detection limit of the assay.

Purified Cthrc1 was radiolabeled with $^{125}$I and infused into anesthetized Cthrc1 deficient mice via the left carotid artery. Using the clearance curve, the half-life of Cthrc1 in plasma was calculated to be 146 minutes (GraphPad Prism software, FIG. 4).

Example 3. Expression of Cthrc1 in Remodeling Arteries

Immunohistochemistry for Cthrc1 was performed on newborn pups (1 day old) of wild-type and Cthrc1 deficient mice. In addition, a growing testicular germ cell tumor was also examined for Cthrc1 expression. After birth the cardiovascular system undergoes dramatic changes. These changes include increased perfusion of the lung, closure of the foramen ovale, closure of the ductus arteriosus, and regression of the umbilical vessels. In addition, blood pressure increases gradually from systolic 40-50 mm Hg in late stage fetuses (Moscoso et al., 1983; Struijk et al., 2008) requiring extensive vascular remodeling.

Prominent expression of Cthrc1 was observed in mural cells of many blood vessels, especially pericytes of postcapillary venules (FIGS. 5A and 5B) as well as in cells of the adventitia surrounding smooth muscle cells of muscular veins and elastic arteries (FIG. 5D-5F). In the ductus arteriosus undergoing closure, Cthrc1 was expressed by most smooth muscle cells (FIG. 5D). Abundant immunoreactive Cthrc1 could also be seen in blood filling the lumen of venules (FIG. 5B). The rabbit monoclonal anti-Cthrc1 antibody that was used for immunohistochemistry is specific and does not react with any proteins in Cthrc1 deficient mice (FIG. 5C). Connective tissue surrounding the umbilical vessels and cells of the outer layer of the umbilical artery revealed strong expression of Cthrc1 (FIG. 5E). Cthrc1 was also induced in adventitial cells of the rat carotid artery after balloon injury (Pyagay et al., 2005). Cthrc1 is a secreted protein (Pyagay et al., 2005), and the appearance of immunoreactive Cthrc1 in an ER-Golgi/secretory vesicle type pattern reflected this fact (FIGS. 5A-H).

The major sites of Cthrc1 expression were pericytes in postcapillary venules and adventitial cells adjacent to smooth muscle cells of the tunica media in larger vessels undergoing remodeling. Many venules in the brain revealed immunoreactive Cthrc1 within the lumen and, without being bound to a particular theory, one possibility is that Cthrc1 expressed by pericytes contributes to circulating levels of Cthrc1 detected in human plasma. The pharmacokinetic studies performed with radiolabeled Cthrc1 are in support of Cthrc1 as a circulating factor with systemic effects. In addition, Cthrc1 expressed by adventitial cells surrounding the tunica media of larger vessels could have direct effects on adjacent medial smooth muscle cells. Without being bound to a particular theory, because Cthrc1 is expressed in remodeling vessels and not in normal vessels, the Cthrc1 promoter may be useful for manipulating gene expression in remodeling blood vessels.

Figure 6:
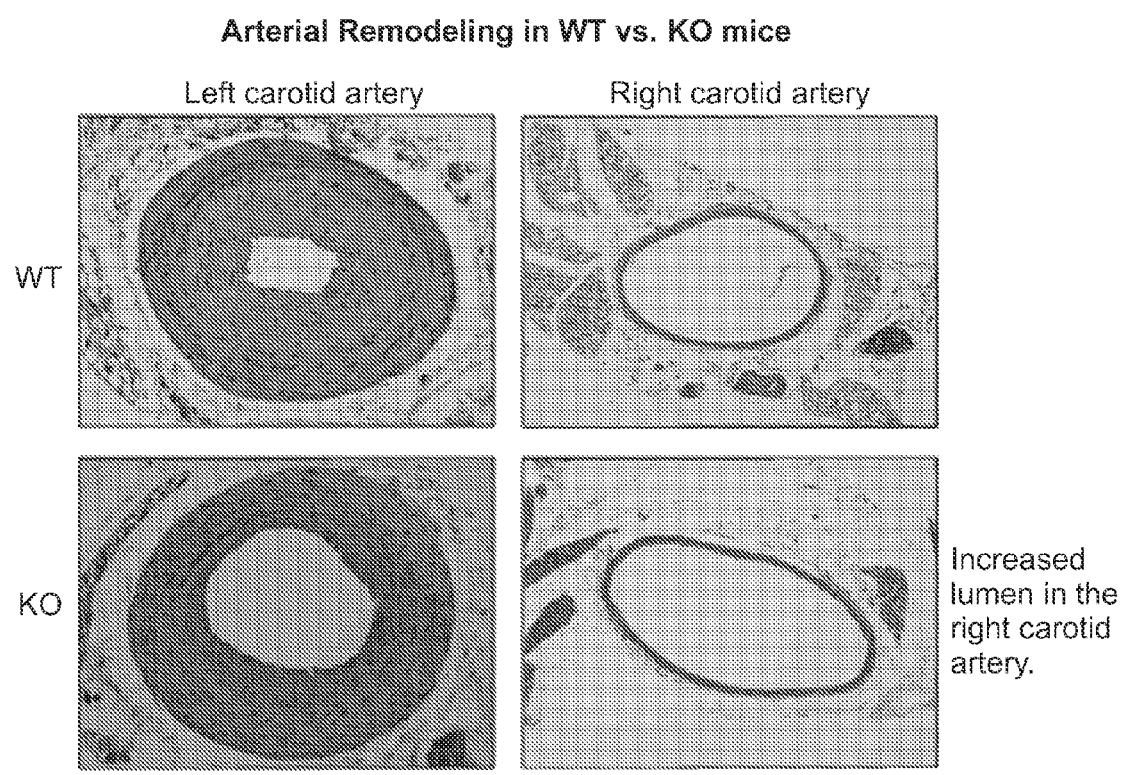
FIG. 6 depicts representative photomicrographs of mouse carotid arteries 4 weeks after ligation of the left carotid artery. In the ligated left carotid artery intimal and medial thickening develops. In Cthrc1$^{-/-}$ mice (KO) but not wildtype mice (WT) the contralateral right common carotid artery undergoes outward remodeling.

Example 4. Increased Flow and Outward Remodeling in Carotid Arteries of Cthrc1 Deficient Mice The carotid artery ligation model and the remodeling response in both the ligated (left) and contralateral non-ligated carotid artery has been described and characterized (Harmon et al., 2000; Kumar and Lindner, 1997). Morphometric analyses of the contralateral carotid arteries revealed a 78% increase in lumen area in Cthrc1 deficient mice (FIG. 6 and Tables 1, 2, 3) whereas there was no change in the wild-type control mice of the 129 background (Harmon et al., 2000). As a separate method to assess vascular remodeling ultrasound was used in live animals. As shown in Table 1, assessment of right carotid arteries from Cthrc1$^{-/-}$ mice and wild-type 129SvEv prior to ligation of the left carotid artery by ultrasound showed no significant differences between groups. In unmanipulated mice lumen diameter and vessel wall thickness of the right common carotid artery as well as blood flow were similar in wild-type and Cthrc1 deficient mice. Assessment of right carotid arteries from Cthrc1$^{-/-}$ mice 129SvEv four weeks after ligation of the left carotid artery by ultrasound showed extensive outward remodeling in Cthrc1$^{-/-}$ mice with an increase in vessel diameter and a significant increase in blood flow (Table 2). Although a significant increase in vessel diameter was observed in Cthrc1$^{-/-}$ mice but not in wild-type mice (Table 2), blood flow increased in both wild-type and Cthrc1$^{-/-}$ mice. However, compared to pre-ligation levels, blood flow in the non-ligated carotid increased only 1.7 fold in wild-type mice compared to 3.2 fold in Cthrc1$^{-/-}$ (Tables 1, 2). As shown in Table 3, vessels from Cthrc1$^{-/-}$ mice revealed a large increase in lumen area whereas wild-type vessels did not (see also Table 1 and 2).

TABLE 1

Assessment of right carotid arteries from Cthrc1$^{-/-}$ mice and wild-type 129SvEv prior to ligation of the left carotid artery by ultrasound.

|  | 129SvEv (n = 4) | Cthrc1-/- (n = 4) |  |
| --- | --- | --- | --- |
| Right Carotid Artery Diameter (systolic, mm, mean ± SD) | 0.684 ± 0.01 | 0.651 ± 0.03 | N.S. |
| Right Carotid Artery Diameter (diastolic, mm, mean ± SD) | 0.587 ± 0.02 | 0.559 ± 0.01 | N.S. |
| Right Carotid Artery wall thickness (systolic, mm, mean ± SD) | 0.070 ± 0.010 | 0.061 ± 0.010 | N.S. (p = 0.155) |
| Right Carotid Artery Mean Flow During Systole, mm$^2$/s, mean ± SD) | 22.75 ± 7.18 | 31.56 ± 12.25 | N.S. |
| Right Carotid Artery Mean Flow During Diastole, mm$^2$/s, mean ± SD) | 16.25 ± 5.13 | 22.13 ± 7.84 | N.S. |
| Heart Rate (mean ± SD) | 431 ± 55 | 424 ± 42 | N.S. |

TABLE 2

Assessment of right carotid arteries from Cthrce" mice and wild-type 129SvEv four weeks after ligation of the left carotid artery by ultrasound.

|  | 129SvEv (n = 4) | Cthrc1-/- (n = 4) |  |
| --- | --- | --- | --- |
| Right Carotid Artery Diameter (systolic, mm, mean ± SD) | 0.651 ± 0.05 | 0.727 ± 0.01 | P = 0.03 |
| Right Carotid Artery wall thickness (systolic, mm, mean ± SD) | 0.075 ± 0.010 | 0.072 ± 0.010 | N.S. |
| Right Carotid Artery Mean Flow During Systole, mm$^2$/s, mean ± SD) | 38.76 ± 15.42 | 101.89 ± 30.08 | P = 0.01 |

TABLE 2-continued

Assessment of right carotid arteries from Cthrce" mice and wild-type 129SvEv four weeks after ligation of the left carotid artery by ultrasound.

|  | 129SvEv (n = 4) | Cthrc1−/− (n = 4) |  |
|---|---|---|---|
| Right Carotid Artery Mean Flow During Diastole, mm²/s, mean ± SD) | 27.91 ± 22.13 | 72.65 ± 25.90 | P = 0.02 |
| Heart Rate (mean ± SD) | 446 ± 32 | 470 ± 51 | N.S. |

TABLE 3

Morphometric analyses performed on sections of perfusion fixed right carotid arteries 4 weeks after ligation of the left carotid.

|  | 129SvEv (n = 5) | Cthrc1−/− (n = 5) |  |
|---|---|---|---|
| Right Carotid Artery Lumen Area (μm² ± SEM) | 88545 ± 7532 | 157568 ± 17008 | P = 0.01 |
| Right Carotid Artery Medial Area (μm² ± SEM) | 17532 ± 1176 | 21279 ± 2920 | P = 0.236 |

For the carotid artery ligation model, typically the attention is focused on the ligated carotid artery undergoing constrictive remodeling with formation of expansive neointimal thickening caused by smooth muscle proliferation and migration. In most strains including the 129J strain there is no significant change in morphometric parameters of the contralateral right carotid artery as determined by histomorphometry of artery cross-sections (Harmon et al., 2000). Using in vivo high resolution ultrasound, it was confirmed that the vessel diameter does not change in the right carotid artery of wild-type mice, whereas flow through the vessel was increased significantly. In Cthrc1−/− mice, however, vessel diameter of the non-ligated carotid artery increased significantly and the concomitant increase in flow was even more dramatic (Table 1 and 2) compared to wild-type mice. The data suggest that the observed increase in flow in the non-ligated carotid artery could even overcompensate for the lack of flow to the head through the left carotid artery.

In addition to increased collateral formation and vascular outward remodeling in Cthrc1 deficient mice following vascular manipulations, the results provide evidence for increased tissue perfusion at baseline. For example, magnetic resonance angiography and imaging of the liver indicates larger hepatic vessels with increased flow. Furthermore, blood flow in the right carotid artery was approximately 40% higher in unmanipulated Cthrc1−/− mice compared to wild-type mice (Table 1), even though with n=4 mice per group this was not statistically significant.

Example 5. Accelerated Recovery of Cthrc1−/− Mice in the Hindlimb Ischemia Model Ctrhrc1−/− and wild-type mice were subjected to experimental hindlimb ischemia by ligation and dissection of the femoral artery below the inguinal ligament. The formation of collateral blood flow and perfusion was monitored longitudinally by MRA. Cthrc1 deficient mice recovered more quickly than wild type controls as determined by re-establishment of perfusion and resolution of muscle edema (FIG. 7A, 7B).

Cthrc1 null mice show larger blood vessel diameter in the angiograms compared to WT and Cthrc1 overexpressing mice. Cthrc1−/− mice are also able to re-connect the excised femoral artery at 10 days post ligation, 4 days sooner than wild-type (WT) and Cthrc1 overexpressing mice (red squares in (FIG. 7A)). In addition, Cthrc1 null group re-established blood flow to the ischemic muscle area 7 days sooner than WT or Cthrc1 overexpressing mice (FIG. 7B). The bright muscle area in (FIG. 7B) has recovered within 7 days post surgery in Cthrc1−/− mice, suggesting collateral formation that is not detected by the MR angiography.

The remodeling response in Cthrc1−/− observed in the hindlimb ischemia model surprisingly showed extensive collateral formation occurred earlier compared to wild-type and Cthrc1 overexpressing mice. In addition, edema in the calf muscles caused by the ischemia was completely resolved in Cthrc1−/− mice within 7 days after femoral artery ligation, whereas it took wild-type mice and Cthrc1 overexpressing mice more than 10 days to recover (FIG. 7B).

Figure 13:
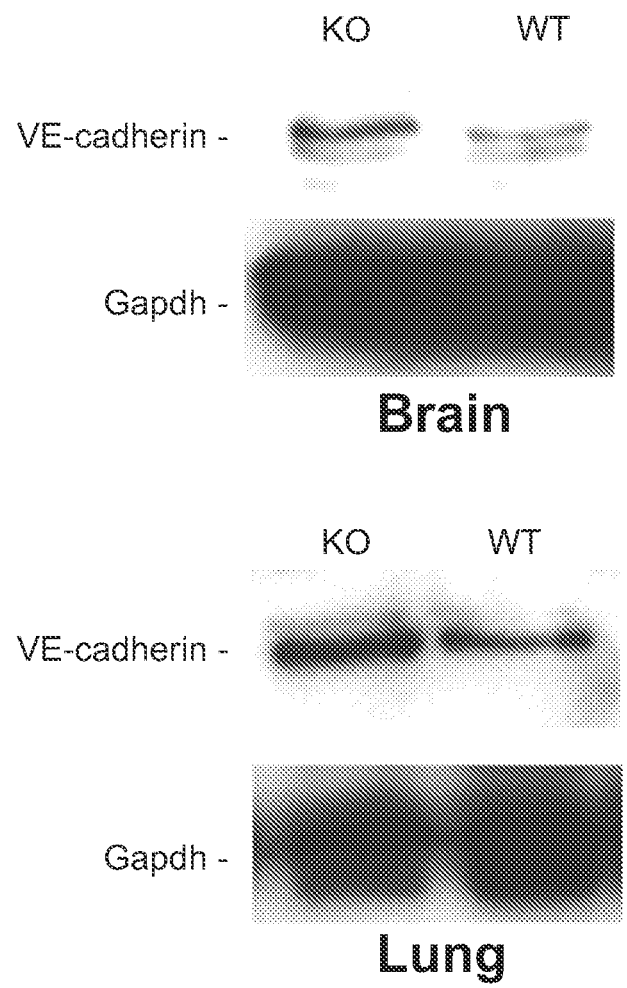
FIG. 13 depicts an increase in levels of the endothelial cell specific marker VEcadherin (cadherin-5) in brain. Western blot analyses of lung and brain tissues from Cthrc1−/− and wild-type mice were used to determine the relative endothelial cell content in various organs as evidence of vascularization.

Rabbit antisera against the endothelial cell specific marker VE-cadherin (cadherin-5) was generated and used to determine the relative endothelial cell content in various organs as a read-out of vascularization using Western blot analysis. Organs from wild-type and Cthrc1−/− mice were harvested after extensive perfusion with phosphate-buffered saline to remove as much blood from tissues as possible. Total protein (100 μg) from tissue from the harvested organs was immunoblotted for VE-cadherin. Lung and brain from Cthrc1−/− mice revealed considerably higher levels of VE-cadherin, indicating increased vascularization compared to wild-type mice (FIG. 13). Thus, accelerated recovery from hindlimb ischemia is due in part to increased vascularization of tissues.

The data demonstrate that Cthrc1 functions as an endogenous inhibitor of vascularization, vascular outward remodeling and collateral formation. Without being bound to theory, therapies targeting inhibition of Cthrc1 function or expression hold great promise for improving any medical condition that is caused by inadequate tissue perfusion.

Example 6. Dilated Veins in Cthrc1−/− Mice

Figure 8:
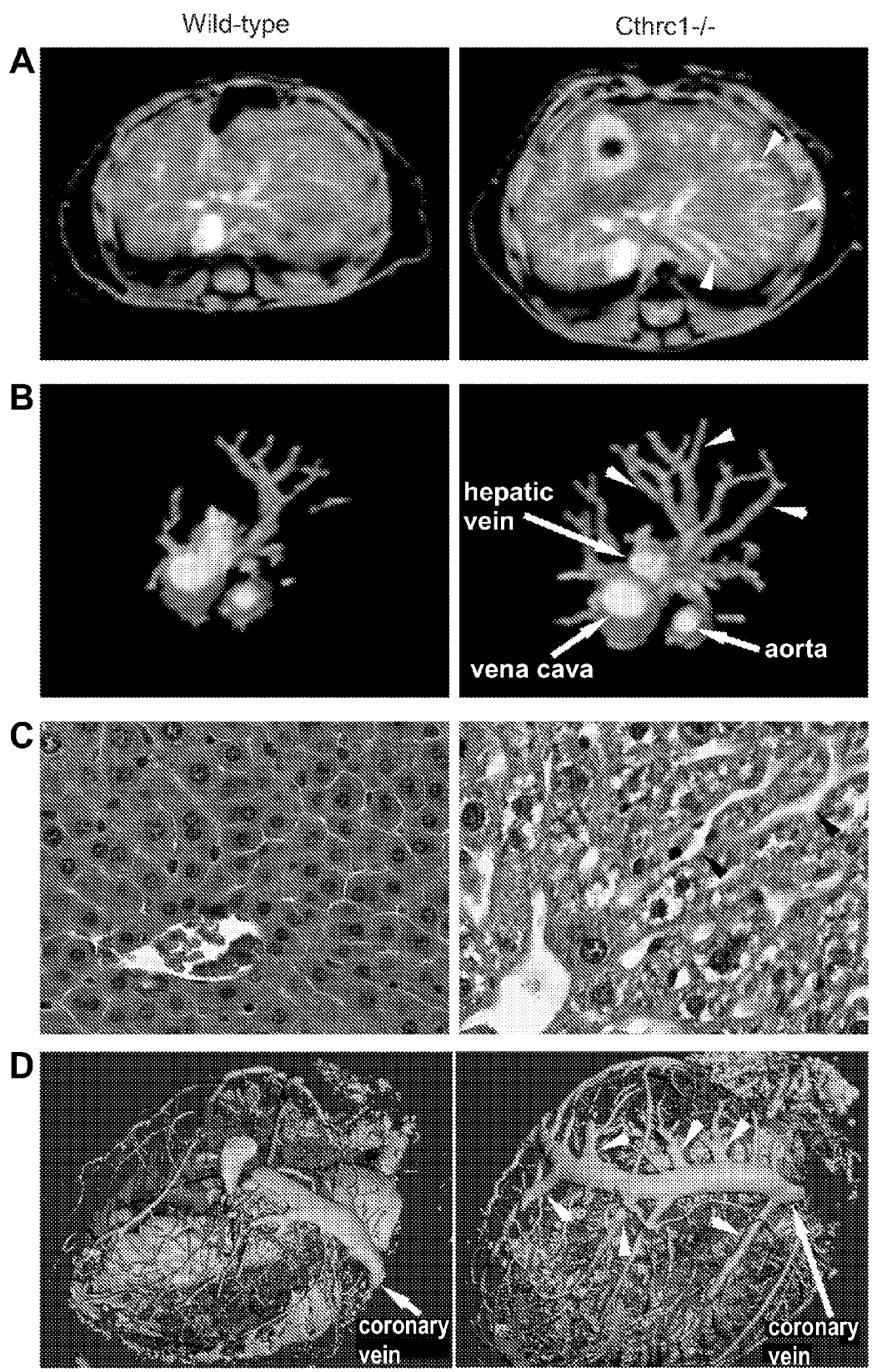
FIG. 8A, FIG. 8B, and FIG. 8C depict representative magnetic resonance images and magnetic resonance angiograms of wild type (WT) and CTHRC1−/− livers with corresponding histology.
FIG. 8D depicts vascular casts imaged by microCT using silicone rubber injection compounds (Microfil®) infused into the left ventricle of the heart. The analysis of the casts by microCT produces a three-dimensional reconstruction of the vasculature with the mutant heart showing extensive dilation of veins feeding into the left coronary vein.

Imaging of the liver vasculature by magnetic resonance imaging (MRI) showed higher signal intensity in Cthrc1−/− mice in T1 weighted images indicating dilation of the vessels (FIG. 8A). The increased vessel volume also led to better 3D reconstruction of the vascular bed in the magnetic resonance angiograms (MRA, FIG. 8B). Histology of livers from wild-type (WT) and Cthrc1−/− mice revealed dilated hepatic vessel and sinuses in the mutant mice (FIG. 8C) suggestive of increased perfusion. Using microCT analysis on vascular casts prepared from hearts also revealed dilated veins feeding into coronary veins (FIG. 8D).

Example 7. Cthrc1 Reduces Nitric Oxide Synthase Levels

Figure 9B:
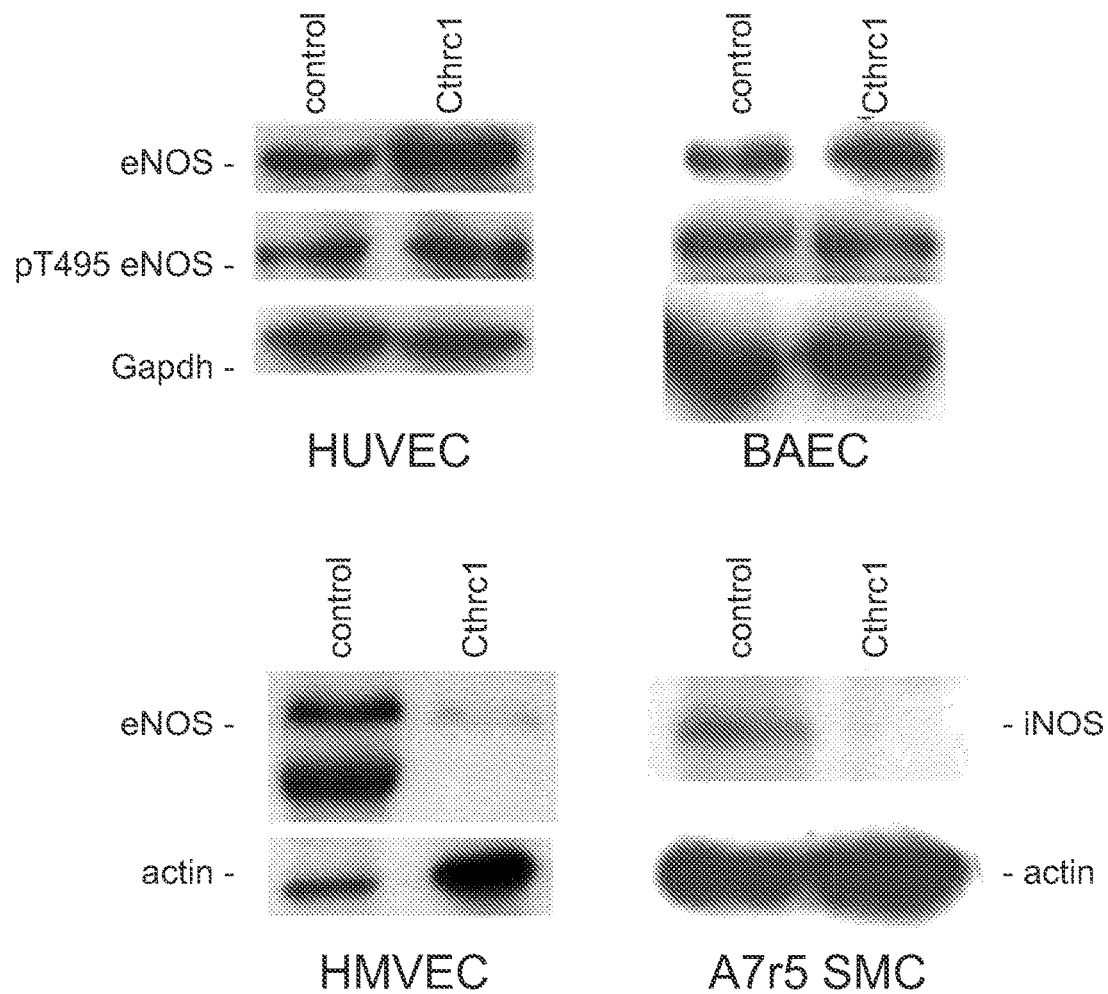
FIG. 9B shows reduced levels of eNOS expression in primary endothelial cells transduced with a Cthrc1 expressing adenovirus.

The most significant factor currently known to regulate arteriogenesis during the recovery from hindlimb ischemia is inducible nitric oxide synthase (iNOS) (Troidl et al., 2010) Inhibition of all isoforms of NOS by L-NAME prevents collateral artery growth following femoral artery ligation. Thus, the production of NO is essential for arteriogenesis. Accelerated recovery from femoral artery ligation in Cthrc1−/− mice therefore led to the examination of NOS isoform levels in Cthrc1−/−, wild-type, and Cthrc1 transgenic mice. In all organs that expressed detectable levels of the constitutive isoforms of NOS, eNOS and nNOS, enzyme expression levels were reduced in Cthrc1 overexpressing mice compared to wild-type and Cthrc1$^{-/-}$ mice, which had similar levels (FIG. 9A). In brains from adult mice, iNOS was detected by Western blot analysis, and in Cthrc1 overexpressing mice the levels of this inducible NOS isoform were reduced (FIG. 9A).

eNOS is expressed constitutively be endothelial cells in vitro. Levels of eNOS in endothelial cells derived from large vessels, human umbilical veins (HUVEC) and bovine aortae (BAEC), were not affected by Cthrc1 overexpression (FIG. 9B). Transduction of human microvasculature derived endothelial cells (HMVEC) with adenovirus expressing Cthrc1 resulted in a reduction in eNOS protein levels. Transduction of A7r5 rat smooth muscle cells with adenovirus expressing Cthrc1 also showed a dramatic reduction in LPS-induced iNOS expression in these cells (FIG. 9B).

NOS levels in tissues which constitutively express iNOS isoforms, such as the brain, liver, heart, and aorta, are reduced in mice overexpressing Cthrc1 (FIG. 9A). Without being bound to a particular theory, this observation supports the idea that Cthrc1 functions as an inhibitor of eNOS, nNOS, and iNOS. No differences in brain NOS levels were observed between wild-type and Cthrc1.sup.-/- mice. Without wishing to be bound by theory, this observation could be explained by the absence of Cthrc1 expression in normal adult tissues with no ongoing vascular remodeling (Pyagay et al., 2005). For example, there was no detectable expression of Cthrc1 in normal carotid arteries from adult rats (Pyagay et al., 2005).

Cthrc1 significantly reduced eNOS levels in human microvascular endothelial cells (HMVEC) (FIG. 9B) but not in human umbilical vein endothelial cells (HUVEC) or bovine aortic endothelial cells (BAEC). A7r5 smooth muscles transduced with a Cthrc1 expressing adenovirus showed reduced levels of iNOS in response to stimulation with lipopolysaccharide (LPS).

Figure 10A:
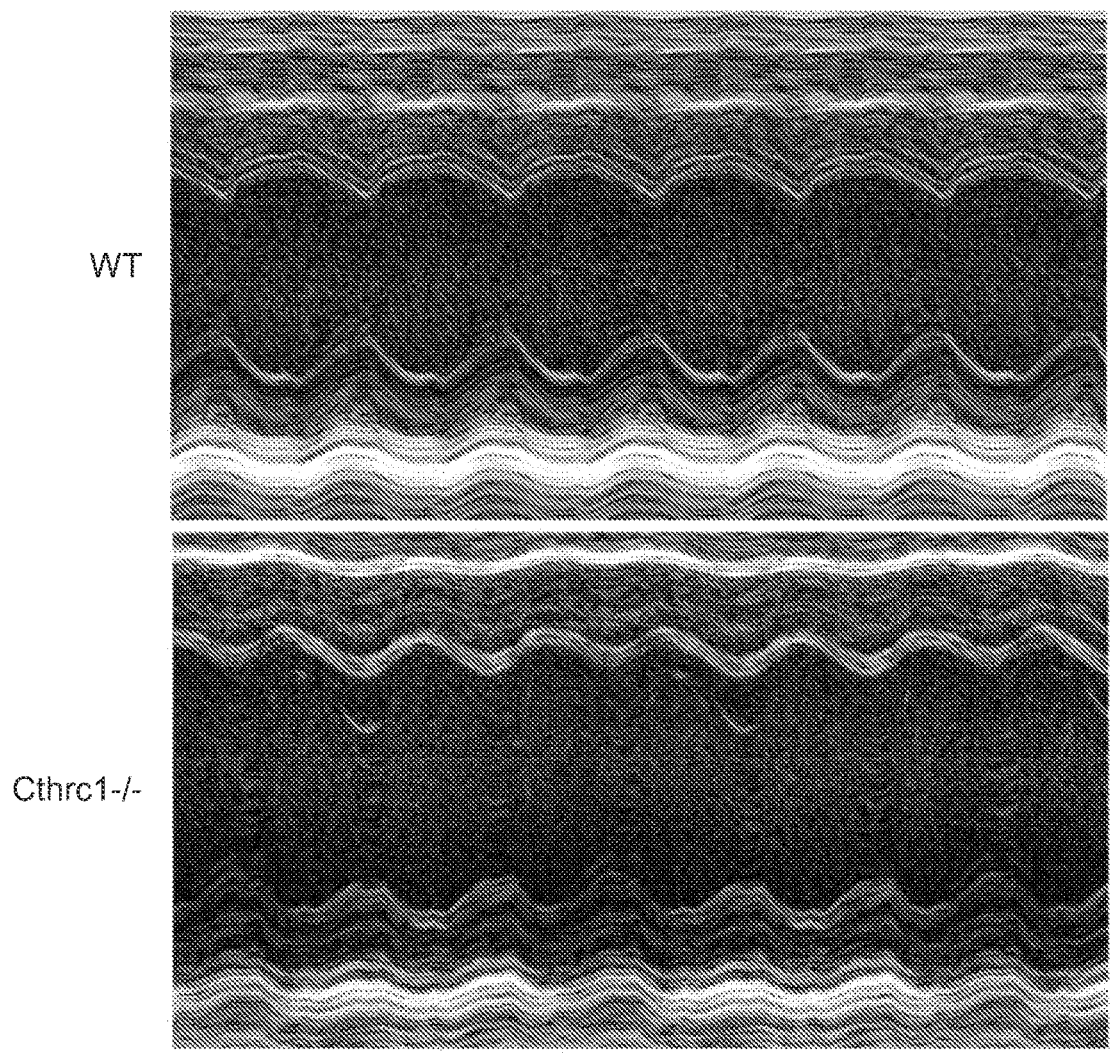
Figure 11:
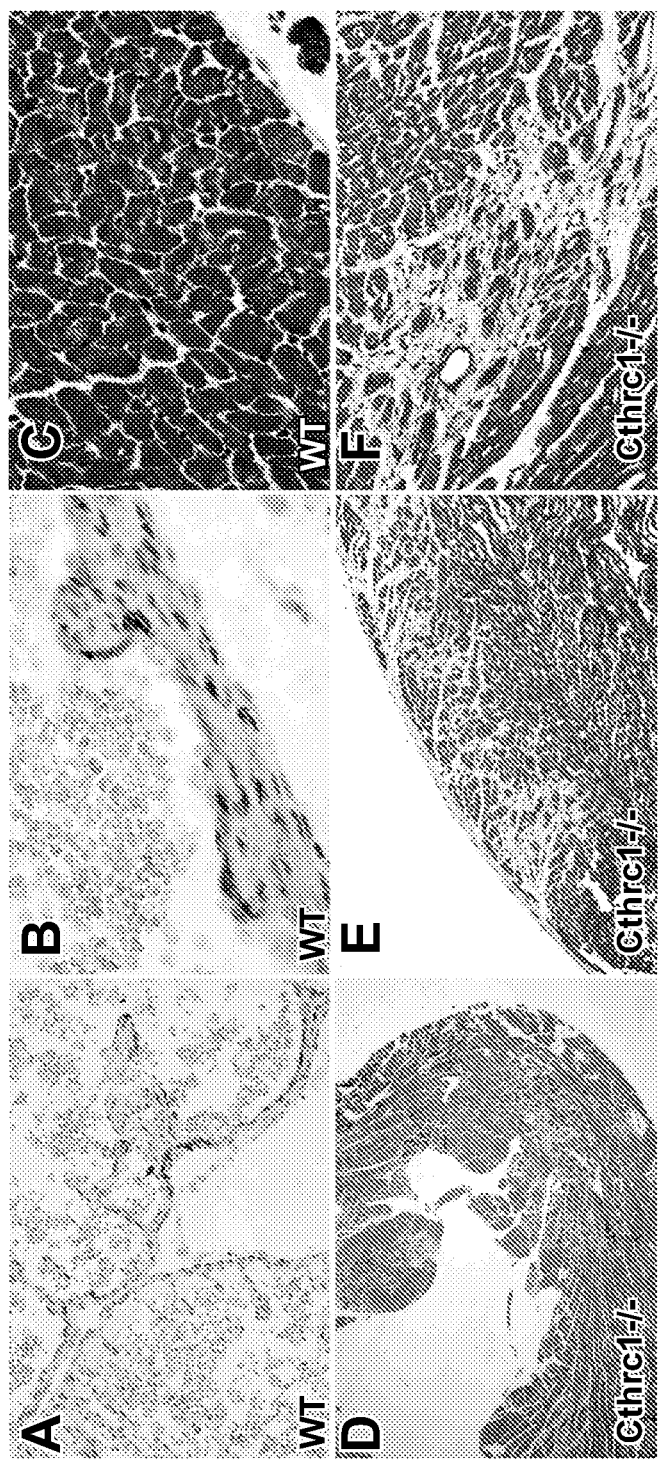
FIG. 11A, FIG. 11B, FIG. 11C, FIG. 11D, FIG. 11E, FIG. 11F depict expression of Cthrc1 in wild type mice and histopathology of advanced cardiomyopathy in a Cthrc1−/− mutant.
Figure 12:
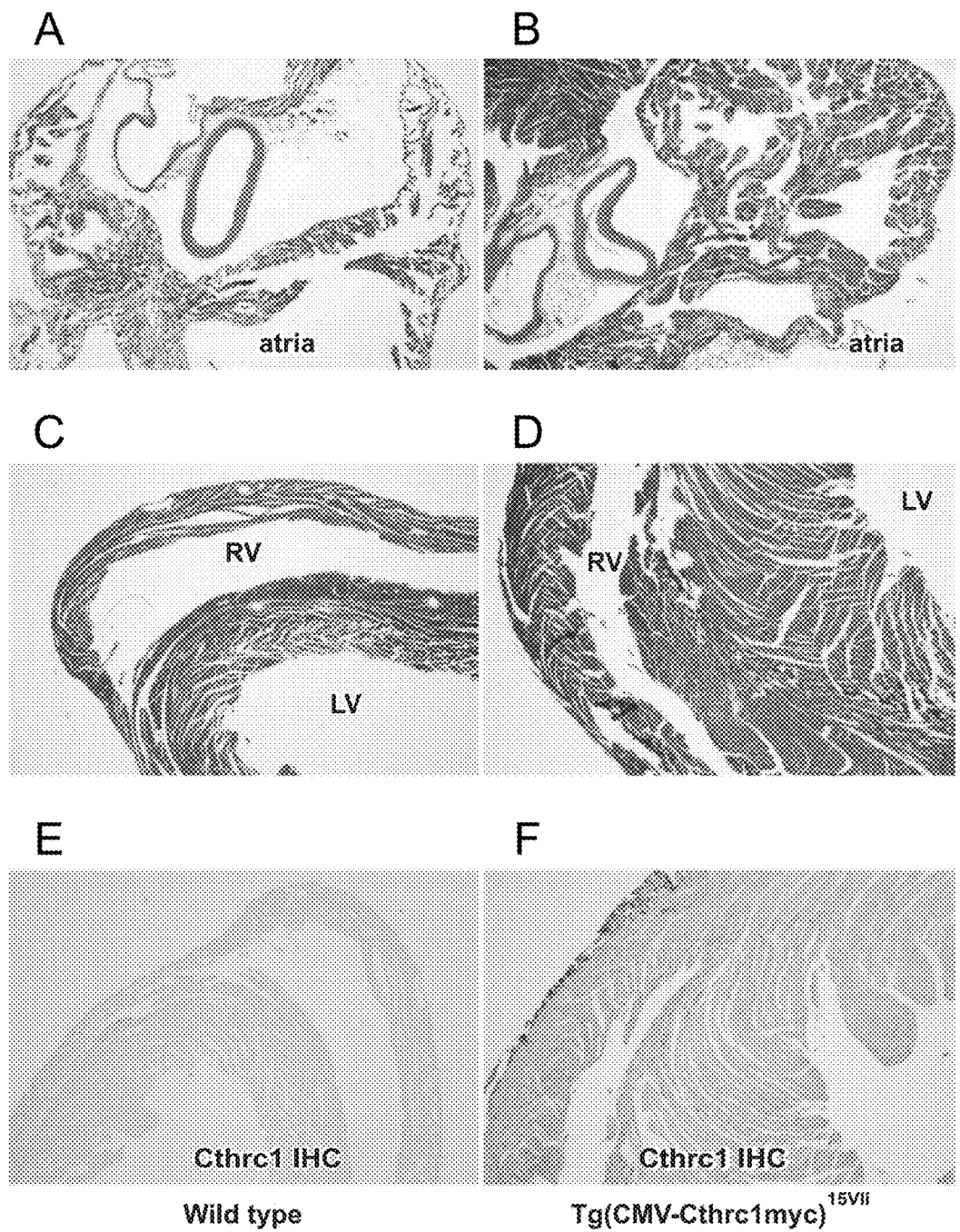
FIG. 12A, FIG. 12B, FIG. 12C, FIG. 12D, FIG. 12E, and FIG. 12F depict cardiac hypertrophy in transgenic mice constitutively overexpressing Cthrc1. Histology of a heart from a Cthrc1 overexpressing strain Tg(CMVCthrc1myc) 15V1i and corresponding wild type littermate is shown. There is hypertrophy of all cardiac chambers. Immunohistochemstry (IHC) with the anti-myc MMC3-47 antibody demonstrates overexpression of the transgene in the myocardium.

Example 8. Cthrc1 Deficient Mice Show a Decline in Cardiac Function with Age Macroscopic examination of hearts from Cthrc1$^{-/-}$ mice several months old demonstrated enlargement of the ventricles. Typical left ventricle (LV) echocardiographic M-mode images were used to analyze LV morphology and function in vivo (FIG. 10A). Cthrc1$^{-/-}$ mice younger than 5 weeks of age did not show LV remodeling or dysfunction and had a similar cardiac phenotype and function compared to matched wild type mice (WT). As shown in Table 4, Cthrc1 deficient mice have decreased cardiac function at 11 weeks of age with a significant reduction in the ejection fraction (EF) and a dilation of the ventricle as seen by the increases in endsystolic—(ESV) and endodiastolic volume (EDV). SV=stroke volume. Means±SE, *p≤0.05 t-test, compared to age matched WT mice. However, by 11 weeks of age, Cthrc1$^{-/-}$ mice developed LV dilatation and systolic contractile dysfunction (FIG. 10A and Table 4). The maintained ejection fraction suggests compensated adaptation at this age.

TABLE 4

In vivo echocardiographic left ventricular morphology and function in wild type and Cthrc1$^{-/-}$ mice.

| | Wild type 4♀ | Cthrc1$^{-/-}$ 4♀ 11 weeks |
|---|---|---|
| Heart rate (bpm) | 342 ± 15 | 345 ± 29 |
| ESV (μl) | 19.5 ± 5.4 | 33.9 ± 4.6* |
| EDV (μl) | 43.2 ± 7.6 | 64.2 ± 6.1* |
| SV (μl) | 23.7 ± 2.2 | 30.3 ± 2.2* |
| EF (%) | 55.4 ± 5.1 | 47.3 ± 3.1* |

EF = ejection fraction;
ESV = endsystolic volume;
EDV = endodiastolic volume;
SV = stroke volume.
Means ± SE,
*p ≤ 0.05 t-test, compared to age matched WT mice.

The in vivo diastolic function assessment included the measurement of flow through the mitral valve (FIG. 10B). At 6 weeks of age the E/A ratio is similar between WT and Cthrc1.sup.-/- hearts. However, at 9 weeks of age the E/A ratio indicates diminished diastolic performance based on the missing or diminished A peak representing the atrial contraction. Histological examination of a hearts from 8 month old Cthrc1.sup.-/- mice exhibited dilation and focal areas of fibrosis (FIG. 11A-11D).

Example 9. Cthrc1 is Expressed in Heart Undergoing Cardiac Remodeling

The cardiac phenotype in Cthrc1 deficient mice raised the question whether Cthrc1 is expressed in the heart. Previous analyses of Cthrc1 mRNA expression by Northern blotting in our laboratory[1, 3] and by Kimura et al.[5] showed no detectable expression of Cthrc1 in normal heart. Endogenous Cthrc1 protein, however, was detectable in the left atrium of the heart in newborn mice. The cardiovascular system undergoes extensive remodeling after birth. With the ductus arteriosus and the formamen ovale closing after birth the left atrium is experiencing a dramatic increase in blood volume that needs to be pumped into the left ventricle. The expression of Cthrc1 in the left atrium coincided with this remodeling event.

Example 10. Overexpression of Cthrc1 in Transgenic Mice Causes Cardiac Hypertrophy The deteriorating cardiac function observed in Cthrc1 deficient mice, raised the question of whether chronic overexpression of Cthrc1 would affect the heart. Transgenic mice overexpressing Cthrc1 under the control of the CMV promoter were previously shown to overexpress Cthrc1 in various organs. These mice also overexpress Cthrc1 in the myocardium as demonstrated by immunohistochemistry with an antibody recognizing the myc epitope tag (FIG. 12A, FIG. 12B, FIG. 12C, FIG. 12D, FIG. 12E, and FIG. 12F). These mice showed hypertrophy of all 4 chambers of the heart at 10 months of age (FIG. 12A, FIG. 12B, FIG. 12C, FIG. 12D, FIG. 12E, and FIG. 12F).

Example 11. Cthrc1 Increases Cardiac Performance and Coronary Flow

The isolated isovolumic heart model was chosen to investigate the effects of Cthrc1 on cardiac function[8]. Cardiac function in response to Cthrc1 or control medium was tested.

Cthrc1 was added to the coronary flow at a final concentration of 6 ng/ml. After an equlibration period the control conditioned medium was added to the coronary flow at 3% of the total coronary flow. No significant changes in measured parameters were observed (Table 5). Cthrc1 had no effects on heart rate, but significantly increased cardiac contractility, cardiac work, and coronary flow, while also causing faster relaxation. Within three minutes of adding Cthrc1-containing conditioned medium to the coronary flow (final Cthrc1 concentration in the coronary perfusate was 6 ng/ml), however, the heart responded with a significant increase in developed pressure and contractility (pdP/dt, Table 5). In addition, faster relaxation (ndP/dt) and an increase in coronary flow were also observed, whereas heart rate remained unaffected (Table 5). These findings indicate that Cthrc1 has positive inotropic and ionotropic effects, as well as coronary flow increasing effects, and that delivery of Cthrc1 to the circulation has an effect on cardiac function.

TABLE 5

Cardiotropic effects of Cthrc1.

|  | Baseline | Control medium | Post Cthrc1 medium | % change from baseline | % change from control |
|---|---|---|---|---|---|
| EDP (mmHg) | 7.5 ± 0.4 | 7.3 ± 0.2 | 7.8 ± 0.2 | 4 | 7 |
| SP (mmHg) | 98 ± 7 | 103 ± 4 | 118 ± 6* | 20 | 14 |
| HR (BPM) | 330 ± 7 | 301 ± 11 | 317 ± 12 | −6 | 2 |
| ndP/dt (mmHg/s) | 1778 ± 131 | 1969 ± 95 | 2420 ± 106* | 36 | 23 |
| pdP/dt (mmHg/s) | 3068 ± 176 | 3331 ± 102 | 3968 ± 120* | 29 | 19 |
| CF (ml/min) | 1.60 ± 0.04 | 1.72 ± 0.14 | 2.13 ± 0.07* | 33 | 24 |
| devP (mmHg) | 91 ± 7 | 96 ± 4 | 110 ± 6* | 21 | 14 |

Parameters of diastolic function: EDP=end diastolic pressure; ndP/dt=first derivative of pressure drop, a measure for calcium reuptake into the SR. Parameters of systolic function: SP=systolic pressure; pDP/dt=first derivative of pressure generation, a measure for contractility and calcium release; developed pressure (devP)=SP−EDP; RPP=rate pressure product, a measure of cardiac pressure generation. HR=heart rate, CF=coronary flow. Data are means±SE, n=5, *p<0.05 (ANOVA for repeated measurements), Student Newman Keul's posthoc comparison.

Example 12. Methods of Screening for Compounds that Compete for Binding with Cthrc1

Binding of Cthrc1 to its receptor in heart provides a desirable outcome, increasing cardiac output without increasing cardiac rate. Therefore, cardiac output is increased without substantially increasing oxygen consumption which is important particularly in a subject already experiencing cardiac insufficiency, either acutely or chronically. Having identified a useful activity of Cthrc1 in heart, Cthrc1 and/or Cthrc1 fragments can be used to compete for binding of Cthrc1 to its receptor. The receptor is most likely a cell surface receptor. A binding assay can be developed using an enriched membrane fraction from cells known to bind Cthrc1. Having defined a membrane fraction to which Cthrc1 binds, a competition assay can be performed using labeled Cthrc1. Cthrc1 bound to the membrane can be determined using a filter binding assay in which unbound Cthrc1 is washed through the membrane, and Cthrc1 bound to the membrane does not wash through the filter. Such methods are well known to those of skill in the art. Competition assays can be performed by combining the membranes, the Cthrc1, and the agent to be tested for binding to the receptor in a single container. An agent that decreases binding of Cthrc1 to the membrane is a candidate for binding to the same receptor.

Alternatively, an in vitro screening assay can be performed to characterize and identify the receptor. A cDNA expression library is transfected into a suitable cell line. The transfected cells are incubated with myc tagged Cthrc1 followed by flow cytometry cell sorting with the anti-myc monoclonal Vli-1 could be one way to identify the receptor. Upon identification of the receptor, the receptor can be expressed in a cell line using routine methods. Such cells can be cultured in wells and competition assays with a library of agents for binding of Cthrc1 to the cell surface can be performed using routine methods.

The results reported above were obtained using the following methods and materials.

Animal Model of Vascular Remodeling.

Left carotid artery ligation (Kumar and Lindner, 1997) was performed in groups of age- and gender-matched Cthrc1 deficient mice and wild-type mice (n=4-5 mice per group, 12 weeks of age). Ultrasound analysis of the right common carotid artery (not ligated) was performed before ligation of the left carotid artery and again 2-3 days before euthanasia and tissue collection at 28 days after ligation. Mice were perfusion fixed at physiological pressure with 4% paraformaldehyde/1% glutaraldehyde in phosphate buffer. Morphometry of the right common carotid was performed on 3-5 sections per vessel as described (Harmon et al., 2000). Morphometry of the right common carotid was also performed on groups of unmanipulated mice (n=5 mice per group, 12 weeks of age).

Animal Model of Ischemia.

Femoral artery ligation and transection (Helisch et al., 2006) was performed as described (n=3 mice per group, 12 weeks of age). Collateral artery remodeling and perfusion were monitored by magnetic resonance angiography (MRA) and magnetic resonance imaging (MRI) analysis 1, 7, 10, and 14 days after femoral artery ligation.

Ultrasound Study of the Right Common Carotid Artery

In vivo carotid artery ultrasound was performed on 12- and 16-week old mice. Mice were anesthetized with 1% isoflurane/99% oxygen and positioned supine on a platform with temperature control (38±1° C.). Heart rate and respiration were monitored. Carotid artery images and measurements of blood velocity were acquired using a VisualSonics Vevo2100 high-resolution ultrasound scanner and the MS400 transducer head (VisualSonics Inc., Toronto, Ontario, Canada).

Right common carotid arteries were imaged longitudinally and parallel to the horizontal plane. Vessel diameters in systole and diastole were obtained in M-mode. PW Doppler mode was used to evaluate blood velocity in the right common carotid artery using a 60° angle. For analysis, five measurements of each parameter were taken at three different cross sections of the carotid artery and averaged. Means between groups were compared and evaluated for significance using Student's t-test. Flow was calculated using the formula: $0.25 \times \pi \times \text{diameter}^2 \times \text{velocity}$.

Echocardiographic Study of Left Ventricular Morphology and Function.

In vivo cardiac ultrasound was performed on 6-, 9- and 11 week old mice. Mice were anesthetized with 1% isoflurane and positioned supine on a platform with temperature control (37±1° C.). Heart rate and respiration were monitored. Cardiac images and blood velocity were acquired using a VisualSonics Vevo770 high-resolution ultrasound scanner (VisualSonics Inc., Toronto, Ontario, Canada) operated at 30 MHz, which provided both high spatial and temporal resolution necessary to evaluate in vivo left ventricular morphology and function.

Ultrasound data processing: B-mode images were used to determine left ventricular long and short axis views. M-mode images were obtained from the mid-section of the short axis view and were used to evaluate global left ventricular morphology and function. PW Doppler mode was used to evaluate blood velocity through the mitral valve with the scanhead accurately located along the four chamber apical view plane.

Magnetic Resonance Angiography (MRA) and Magnetic Resonance Imaging (MRI)

MR images were acquired in a BRUKER PharmaScan 7 Tesla, 300 MHz, small animal imaging system. Mice were anaesthetized and anesthesia was maintained with 1-2% isoflurane and a flow of 0.8 L $O_2$/min throughout the experiment. Mice were put prone into the animal holder and respiration and body temperature was monitored using the SA Instruments set up. T1 weighted MR Angiograms of the hindlimb were acquired 1, 7, 10, and 14 days after femoral artery ligation using a FLASH-TOF-2D pulse sequence (TR 13 ms, TE 4 ms, matrix 256×256, FOV 30×30 mm, slice thickness 0.3 mm, number of slices 150, interslice distance 0.15 mm, averages 2, total acquisition time 13 min 46 sec). Images were reconstructed to 3D using ParaVision 4.0 surface projection.

For liver examination, mice were put supine into the animal holder and T1 weighted MR images were acquired using a FLASH pulse sequence with fat suppression and respiration gated (TR 165 ms, TE 3.5 ms, matrix 256×256, FOV 30×30 mm, slice thickness 0.8 mm, number of slices 10, interslice distance 0.8 mm, averages 4, total acquisition time 2 min 48 sec). Angiograms of the liver were acquired using a FLASH-TOF-2D pulse sequence (TR 13 ms, TE 4 ms, matrix 256×256, FOV 30×30 mm, slice thickness 0.4 mm, number of slices 50, interslice distance 0.25 mm, averages 2, total acquisition time 4 min 35 sec). Images were reconstructed to 3D using ParaVision 4.0 surface projection.

Alternatively, in some experiments, MR images were acquired in a BRUKER PharmaScan 7 Tesla, 300 MHz, small animal imaging system. Mice were anaesthetized with 3% isoflurane and anesthesia was maintained with 1% isoflurane and a flow of 0.4 L $O_2$/min throughout the experiment. Mice were put supine into the animal holder and respiration and body temperature was monitored using the SA Instruments set up. T1 weighted MR images were acquired using a FLASH pulse sequence with fat suppression and respiration gated (TR 165 ms, TE 3.5 ms, matrix 256×256, FOV 30×30 mm, slice thickness 0.8 mm, number of slices 10, interslice distance 0.8 mm, averages 4, total acquisition time 2 min 48 sec). Angiograms of the liver were acquired using a FLASH-TOF-2D pulse sequence (TR 13 ms, TE 4 ms, matrix 256×256, FOV 30×30 mm, slice thickness 0.4 mm, number of slices 50, interslice distance 0.25 mm, averages 2, total acquisition time 4 min 35 sec). Images were reconstructed to 3D using ParaVision 4.0 surface projection.

Antibody Generation.

Rabbit monoclonal antibodies were generated using conserved Cthrc1 C-terminal and N-terminal sequences. A rabbit monoclonal antibody was raised against C-terminal conserved peptide sequence GDASTGWNSVSRIIIEELP (SEQ ID NO: 1). Clone Vli-77 was found to be suitable for Western blotting and immunohistochemistry on paraffin-embedded paraformaldehyde-fixed tissues, cross-reacting with mouse, rat, pig, and human specimens. Rabbit monoclonal Vli-77 was used at 20 ng/ml for immunohistochemistry as described (Leclair et al., 2008). Sections from 2 week balloon-injured rat carotid arteries (Pyagay et al., 2005) and newborn mice were examined for Cthrc1 expression.

A rabbit monoclonal antibody was raised against the N-terminal conserved peptide sequence VVDLYNGMCLQGPAGV (SEQ ID NO: 2) using the services of Epitomics, Inc. Clone Vli-42 was found to be suitable for Western blotting and immunohistochemistry on paraffin-embedded paraformaldehyde-fixed tissues, cross-reacting with mouse, rat, pig, and human specimens. Rabbit monoclonal Vli-42 was used for Western blotting at 24 ng/ml and at 200 ng/ml for immunohistochemistry.

A rabbit monoclonal antibody was raised against a synthetic peptide corresponding to the myc epitope tag (EQKLISEEDL) (SEQ ID NO: 7). The antibody, clone Vli-47, recognized C terminal myc epitope tags only. It did not recognize N-terminal myc epitopes. This antibody was used to detect the myc tagged transgene in Tg(CMV-Cthrc1myc)15V1i mice by immunohistochemistry on paraffin embedded tissues (dilution 50 ng/ml).

Recombinant Cthrc1 Expression.

An adenovirus was generated expressing rat Cthrc1 with C terminal myc/6×His tag ("6×His" disclosed as SEQ ID NO: 17). CHO cells were transduced with adenovirus and Cthrc1 protein was purified from the conditioned medium with HIS-Select affinity Gel (Sigma) following the supplier's instructions. Silver-stained SDS-PAGE gels demonstrated >95% purity of the purified protein (not shown). The concentration of the purified protein was determined with the BCA protein assay (Pierce) and by comparison with known amounts of purified immunoglobulin light chain on silver stained SDS-PAGE gels.

Purified Cthrc1 was radiolabeled with $^{125}$I using iodination tubes (Pierce) and infused into anesthetized Cthrc1 deficient mice via the left carotid artery. Blood samples were obtained at the indicated times and Cthrc1 levels were determined in a gamma counter. The half-life in circulation was calculated from the clearance curve using GraphPad Prism software (FIG. 4).

Sandwich ELISA for Detection of Cthrc1 in Human Plasma.

Plasma was prepared from EDTA blood drawn from healthy volunteers. 96-well plates (MaxiSorp. Nunc) were coated overnight at 4° C. with rabbit monoclonal antibody clone Vli-42 (2.5 µg/ml in 0.2M sodium bicarbonate buffer, pH9.5). Non-specific binding was blocked with 2% bovine serum albumin (BSA) in Tris-buffered saline containing 0.1% Tween 20 (TBS-T).

Triplicates of plasma samples (100 μl) were incubated in the coated wells for one hour at room temperature, and washed generously with TBS-T before incubating with anti-Cthrc1 mouse monoclonal (clone 16D4; Maine Biotechnology Services, 1 μg/ml). Horse radish peroxidase (HRP) conjugated anti-mouse antibody (Jackson Immunologicals, Inc) was used at a dilution of 1:5000 in TBS-T with 2% BSA.

The colorimetric reaction was performed with o-phenylenediamine in citrate buffer as described 7. A calibration curve was established with recombinant purified Cthrc1. The intra-assay variability was determined to be 3.5% and the inter-assay variability was 5.3%.

Isolated Working Mouse Heart Model.

The methodology has previously described in detail[8]. Serum-free conditioned medium from CHO cells transduced with an adenovirus expressing C terminally myc/6×His tagged ("6×His" disclosed as SEQ ID NO: 17) rat Cthrc1 was added to the coronary flow. The final concentration of Cthrc1 in the coronary flow was 6 ng/ml. Conditioned medium from CHO cells transduced with a beta-galactosidase expressing adenovirus was used as a the control medium.

Patient Plasma for Cthrc1 Identification.

Plasma samples were obtained from patients or volunteers under institutional review board-approved protocols.

Statistical Analysis.

Data are expressed as mean±standard error. Student's t-test was used for US contractile data. P<0.05 was considered significant.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All references, patents, patent applications, and GenBank or other sequence accession numbers mentioned in this specification are hereby incorporated by reference as if they were each incorporated individually.

REFERENCES

The following documents are cited herein.
1. Pyagay P, Heroult M, Wang Q, Lehnert W, Belden J, Liaw L, Friesel R E, Lindner V. Collagen triple helix repeat containing 1, a novel secreted protein in injured and diseased arteries, inhibits collagen expression and promotes cell migration. Circ Res. 2005; 96(2):261-268.
2. LeClair R J, Durmus T, Wang Q, Pyagay P, Terzic A, Lindner V. Cthrc1 is a novel inhibitor of transforming growth factor-beta signaling and neointimal lesion formation. Circ Res. 2007; 100(6):826-833.
3. Leclair R J, Wang Q, Benson M A, Prudovsky I, Lindner V. Intracellular localization of Cthrc1 characterizes differentiated smooth muscle. Arterioscler Thromb Vasc Biol. 2008; 28(7):1332-1338.
4. Yamamoto S, Nishimura O, Misaki K, Nishita M, Minami Y, Yonemura S, Tarui H, Sasaki H. Cthrc1 selectively activates the planar cell polarity pathway of Wnt signaling by stabilizing the Wnt-receptor complex. Dev Cell. 2008; 15(1):23-36.
5. Kimura H, Kwan K M, Zhang Z, Deng J M, Darnay B G, Behringer R R, Nakamura T, de Crombrugghe B, Akiyama H. Cthrc1 is a positive regulator of osteoblastic bone formation. PLoS ONE. 2008; 3(9):e3174.
6. Durmus T, Leclair R J, Park K S, Terzic A, Yoon J K, Lindner V. Expression analysis of the novel gene collagen triple helix repeat containing-1 (Cthrc1). Gene Expr Patterns. 2006; 6(8):935-940.
7. Floege J, Eng E, Lindner V, Alpers C E, Young B A, Reidy M A, Johnson R J. Rat glomerular mesangial cells synthesize basic fibroblast growth factor. Release, upregulated synthesis, and mitogenicity in mesangial proliferative glomerulonephritis. J Clin Invest. 1992; 90(6):2362-2369.
8. Pinz I, Wax S D, Anderson P, Ingwall J S. Low overexpression of TNFalpha in the mouse heart increases contractile performance via TNER1. J Cell Biochem. 2008. Harmon K J, Couper L L, Lindner V. 2000. Strain-dependent vascular remodeling phenotypes in inbred mice. Am J Pathol 156:1741-1748.
9. Helisch A, Wagner S, Khan N, Drinane M, Wolfram S, Heil M, Ziegelhoeffer T, Brandt U, Pearlman J D, Swartz H M, Schaper W. 2006. Impact of mouse strain differences in innate hindlimb collateral vasculature. Arterioscler Thromb Vasc Biol 26:520-526.
10. Kumar A, Lindner V. 1997. Remodeling with neointima formation in the mouse carotid artery after cessation of blood flow. Arterioscler Thromb Vasc Biol 17:2238-2244.
11. Landry D B, Couper L L, Bryant S R, Lindner V. 1997. Activation of the NF-kappa B and I kappa B system in smooth muscle cells after rat arterial injury. Induction of vascular cell adhesion molecule-1 and monocyte chemoattractant protein-1. Am J Pathol 151:1085-1095.
12. Mees B, Wagner S, Ninci E, Tribulova S, Martin S, van Haperen R, Kostin S, Heil M, de Crom R, Schaper W. 2007. Endothelial nitric oxide synthase activity is essential for vasodilation during blood flow recovery but not for arteriogenesis. Arterioscler Thromb Vasc Biol 27:1926-1933.
13. Moscoso P, Goldberg R N, Jamieson J, Bancalari E. 1983. Spontaneous elevation in arterial blood pressure during the first hours of life in the very-low-birth-weight infant. J Pediatr 103:114-117.
14. Pyagay P, Heroult M, Wang Q, Lehnert W, Belden J, Liaw L, Friesel R E, Lindner V. 2005. Collagen triple helix repeat containing 1, a novel secreted protein in injured and diseased arteries, inhibits collagen expression and promotes cell migration. Circ Res 96:261-268.
15. Struijk P C, Mathews V J, Loupas T, Stewart P A, Clark E B, Steegers E A, Wladimiroff J W. 2008. Blood pressure estimation in the human fetal descending aorta. Ultrasound Obstet Gynecol 32:673-681.
16. Troidl K, Tribulova S, Cai W J, Ruding I, Apfelbeck H, Schierling W, Troidl C, Schmitz-Rixen T, Schaper W. 2010. Effects of endogenous nitric oxide and of DETA NONOate in arteriogenesis. J Cardiovasc Pharmacol 55:153-160.
17. Yamamoto S, Nishimura O, Misaki K, Nishita M, Minami Y, Yonemura S, Tarui H, Sasaki H. 2008. Cthrc1 selectively activates the planar cell polarity pathway of Wnt signaling by stabilizing the Wnt-receptor complex. Dev Cell 15:23-36.

We claim:

1. A kit for performing an assay to detect collagen triple helix repeat containing-1 (CTHRC1) polypeptide in a subject sample consisting of two antibodies that selectively bind to a cryptic epitope of the CTHRC1 polypeptide, wherein a first antibody consists of a monoclonal antibody specific for a C-terminal peptide sequence consisting of GDASTG-WNSVSRIIIEELP (SEQ ID NO: 1) and a second antibody consists of a monoclonal antibody specific for an N-terminal peptide sequence consisting of VVDLYNGMCLQGPAGV (SEQ ID NO: 2).

2. The kit of claim 1, wherein at least one of said antibodies is an anti-CTHRC1 rabbit monoclonal antibody.

3. The kit of claim 2, wherein one of said antibodies is an anti-CTHRC1 mouse monoclonal antibody.

* * * * *

UNITED STATES PATENT AND TRADEMARK OFFICE
CERTIFICATE OF CORRECTION

| | |
|---|---|
| PATENT NO. | : 9,718,878 B2 |
| APPLICATION NO. | : 13/578102 |
| DATED | : August 1, 2017 |
| INVENTOR(S) | : Volkhard Lindner et al. |

It is certified that error appears in the above-identified patent and that said Letters Patent is hereby corrected as shown below:

In the Specification

At Column 1, Lines 15-20, the sentence, "This invention was made with government support under grant number HL069182 awarded by the National Institutes of Health and under grant number F32HL091615 awarded by the National Heart, Lung, and Blood Institute. The government has certain rights in the invention."

Should read:
"This invention was made with government support under grant number HL069182 awarded by the National Institutes of Health and under grant number HL091615 awarded by the National Heart, Lung, and Blood Institute. The government has certain rights in the invention."

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 17

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Asp Ala Ser Thr Gly Trp Asn Ser Val Ser Arg Ile Ile Ile Glu
1               5                   10                  15

Glu Leu Pro

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Val Asp Leu Tyr Asn Gly Met Cys Leu Gln Gly Pro Ala Gly Val
1               5                   10                  15

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccactggaaa cctctggagt tg                                           22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aagttcacac aaaggaagcc ccgc                                         24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtgtgttttg aggtgtggtc cc                                           22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 6
tggatgtgga atgtgtgcga gg                                              22

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Gln Lys Leu Ile Ser Glu Glu Asp Leu
1               5                   10

<210> SEQ ID NO 8
<211> LENGTH: 243
<212> TYPE: PRT
<213> ORGANISM: Homo sapiens

<400> SEQUENCE: 8

Met Arg Pro Gln Gly Pro Ala Ala Ser Pro Gln Arg Leu Arg Gly Leu
1               5                   10                  15

Leu Leu Leu Leu Leu Leu Gln Leu Pro Ala Pro Ser Ser Ala Ser Glu
                20                  25                  30

Ile Pro Lys Gly Lys Gln Lys Ala Gln Leu Arg Gln Arg Glu Val Val
            35                  40                  45

Asp Leu Tyr Asn Gly Met Cys Leu Gln Gly Pro Ala Gly Val Pro Gly
50                  55                  60

Arg Asp Gly Ser Pro Gly Ala Asn Val Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val Glu Gly Leu Cys Glu Gly Ile Gly Ala Gly Leu
        195                 200                 205

Val Asp Val Ala Ile Trp Val Gly Thr Cys Ser Asp Tyr Pro Lys Gly
    210                 215                 220

Asp Ala Ser Thr Gly Trp Asn Ser Val Ser Arg Ile Ile Ile Glu Glu
225                 230                 235                 240

Leu Pro Lys

<210> SEQ ID NO 9
<211> LENGTH: 732
<212> TYPE: DNA
<213> ORGANISM: Homo sapiens
```

<400> SEQUENCE: 9

```
atgcgacccc agggcccccgc cgcctccccg cagcggctcc gcggcctcct gctgctcctg      60
ctgctgcagc tgcccgcgcc gtcgagcgcc tctgagatcc caagggggaa gcaaaaggcg     120
cagctccggc agagggaggt ggtggacctg tataatggaa tgtgcttaca agggccagca     180
ggagtgcctg gtcgagacgg gagccctggg gccaatgtta ttccgggtac acctgggatc     240
ccaggtcggg atggattcaa aggagaaaag gggaatgtc tgagggaaag ctttgaggag      300
tcctggacac ccaactacaa gcagtgttca tggagttcat tgaattatgg catagatctt     360
gggaaaattg cggagtgtac atttacaaag atgcgttcaa atagtgctct aagagttttg     420
ttcagtggct cacttcggct aaaatgcaga atgcatgct gtcagcgttg gtatttcaca      480
ttcaatggag ctgaatgttc aggacctctt cccattgaag ctataattta tttggaccaa     540
ggaagccctg aaatgaattc aacaattaat attcatcgca cttcttctgt ggaaggactt     600
tgtgaaggaa ttggtgctgg attagtggat gttgctatct gggttggcac ttgttcagat     660
tacccaaaag gagatgcttc tactggatgg aattcagttt ctcgcatcat tattgaagaa     720
ctaccaaaat aa                                                         732
```

<210> SEQ ID NO 10
<211> LENGTH: 244
<212> TYPE: PRT
<213> ORGANISM: Equus caballus

<400> SEQUENCE: 10

```
Met Arg Pro Gln Gly Pro Ala Ala Ala Cys Ser Gln Arg Leu Leu Gly
  1               5                  10                  15

Leu Leu Leu Leu Leu Leu Leu Gln Leu Arg Thr Pro Ser Ser Ala Ser
             20                  25                  30

Glu Thr Pro Lys Gly Lys Gln Lys Ala Leu Leu Arg Gln Arg Glu Val
         35                  40                  45

Val Asp Leu Tyr Asn Gly Met Cys Leu Gln Gly Pro Ala Gly Val Pro
     50                  55                  60

Gly Arg Asp Gly Ser Pro Gly Ala Asn Gly Ile Pro Gly Thr Pro Gly
 65                  70                  75                  80

Ile Pro Gly Arg Asp Gly Phe Lys Gly Glu Lys Gly Glu Cys Leu Arg
                 85                  90                  95

Glu Thr Phe Glu Glu Ser Trp Thr Pro Asn Tyr Lys Gln Cys Ser Trp
            100                 105                 110

Ser Ser Leu Asn Tyr Gly Ile Asp Leu Gly Lys Ile Ala Glu Cys Thr
        115                 120                 125

Phe Thr Lys Met Arg Ser Asn Ser Ala Leu Arg Val Leu Phe Ser Gly
    130                 135                 140

Ser Leu Arg Leu Lys Cys Arg Asn Ala Cys Cys Gln Arg Trp Tyr Phe
145                 150                 155                 160

Thr Phe Asn Gly Ala Glu Cys Ser Gly Pro Leu Pro Ile Glu Ala Ile
                165                 170                 175

Ile Tyr Leu Asp Gln Gly Ser Pro Glu Leu Asn Ser Thr Ile Asn Ile
            180                 185                 190

His Arg Thr Ser Ser Val Glu Gly Leu Cys Glu Gly Ile Gly Ala Gly
        195                 200                 205

Leu Val Asp Ile Ala Ile Trp Val Gly Thr Cys Ser Asp Tyr Pro Lys
    210                 215                 220
```

Gly Asp Ala Ser Thr Gly Trp Asn Ser Val Ser Arg Ile Ile Ile Glu
225                 230                 235                 240

Glu Leu Pro Lys

<210> SEQ ID NO 11
<211> LENGTH: 735
<212> TYPE: DNA
<213> ORGANISM: Equus caballus

<400> SEQUENCE: 11

```
atgcgccccc agggccccgc cgccgcctgc tcgcagcggc tcctcggtct gctgctgctc      60
ctgctgctgc agctgcggac gccgtcgagc gcctccgaga cccccaaggg gaagcaaaag     120
gcgctgctcc ggcagaggga ggtggtggac ctgtataatg gaatgtgctt acaagggcct     180
gcaggggtgc cagggcgaga tgggagccct ggggccaatg gcattcctgg taccccctggg     240
atcccaggtc gggatggatt caaggagaa aaggggaat gcctgaggga aaccttcgag      300
gagtcgtgga cacctaacta caagcagtgt tcgtggagtt cgctgaatta tggcatagat     360
cttgggaaaa ttgcggagtg tacatttaca agatgcgtt cgaacagtgc tctgagagtt     420
ttgttcagtg gctcgcttcg gttaaaatgc agaaacgcat gctgtcagcg ttggtatttc     480
acgttcaatg gagctgaatg ttcaggacct cttcccattg aagctataat ttatttggac     540
caaggaagcc cagaactgaa ttcaacaatt aatattcatc gcacttcttc tgtggaagga     600
ctttgtgaag gaattggtgc cggattagtg gatattgcta tctggttgg tacttgttcc     660
gactacccaa aaggagacgc ctctactgga tggaattcag tgtcccgaat cattatcgaa     720
gaactaccaa aataa                                                     735
```

<210> SEQ ID NO 12
<211> LENGTH: 277
<212> TYPE: PRT
<213> ORGANISM: Rattus norvegicus

<400> SEQUENCE: 12

Met Arg Pro Ala Ala Glu Leu Gly Gln Thr Leu Ser Arg Ala Gly Leu
1               5                   10                  15

Cys Arg Pro Leu Cys Leu Leu Leu Cys Ala Ser Gln Leu Pro His Thr
                20                  25                  30

Met His Pro Gln Gly Arg Ala Ala Ser Pro Gln Leu Leu Leu Gly Leu
            35                  40                  45

Phe Leu Val Leu Leu Leu Leu Leu Gln Leu Ser Ala Pro Ser Ser Ala
        50                  55                  60

Ser Glu Asn Pro Lys Val Lys Gln Lys Ala Leu Ile Arg Gln Arg Glu
65                  70                  75                  80

Val Val Asp Leu Tyr Asn Gly Met Cys Leu Gln Gly Pro Ala Gly Val
                85                  90                  95

Pro Gly Arg Asp Gly Ser Pro Gly Ala Asn Gly Ile Pro Gly Thr Pro
            100                 105                 110

Gly Ile Pro Gly Arg Asp Gly Phe Lys Gly Glu Lys Gly Glu Cys Leu
        115                 120                 125

Arg Glu Ser Phe Glu Glu Ser Trp Thr Pro Asn Tyr Lys Gln Cys Ser
    130                 135                 140

Trp Ser Ser Leu Asn Tyr Gly Ile Asp Leu Gly Lys Ile Ala Glu Cys
145                 150                 155                 160

Thr Phe Thr Lys Met Arg Ser Asn Ser Ala Leu Arg Val Leu Phe Ser
                165                 170                 175

```
Gly Ser Leu Arg Leu Lys Cys Arg Asn Ala Cys Cys Gln Arg Trp Tyr
            180                 185                 190

Phe Thr Phe Asn Gly Ala Glu Cys Ser Gly Pro Leu Pro Ile Glu Ala
            195                 200                 205

Ile Ile Tyr Leu Asp Gln Gly Ser Pro Glu Leu Asn Ser Thr Ile Asn
            210                 215                 220

Ile His Arg Thr Ser Ser Val Glu Gly Leu Cys Glu Gly Ile Gly Ala
225                 230                 235                 240

Gly Leu Val Asp Val Ala Ile Trp Val Gly Thr Cys Ser Asp Tyr Pro
            245                 250                 255

Lys Gly Asp Ala Ser Thr Gly Trp Asn Ser Val Ser Arg Ile Ile Ile
            260                 265                 270

Glu Glu Leu Pro Lys
            275

<210> SEQ ID NO 13
<211> LENGTH: 245
<212> TYPE: PRT
<213> ORGANISM: Mus musculus

<400> SEQUENCE: 13

Met His Pro Gln Gly Arg Ala Ala Pro Pro Gln Leu Leu Gly Leu
1               5                   10                  15

Phe Leu Val Leu Leu Leu Leu Gln Leu Ser Ala Pro Ser Ser Ala
            20                  25                  30

Ser Glu Asn Pro Lys Val Lys Gln Lys Ala Leu Ile Arg Gln Arg Glu
            35                  40                  45

Val Val Asp Leu Tyr Asn Gly Met Cys Leu Gln Gly Pro Ala Gly Val
        50                  55                  60

Pro Gly Arg Asp Gly Ser Pro Gly Ala Asn Gly Ile Pro Gly Thr Pro
65                  70                  75                  80

Gly Ile Pro Gly Arg Asp Gly Phe Lys Gly Glu Lys Gly Glu Cys Leu
            85                  90                  95

Arg Glu Ser Phe Glu Glu Ser Trp Thr Pro Asn Tyr Lys Gln Cys Ser
            100                 105                 110

Trp Ser Ser Leu Asn Tyr Gly Ile Asp Leu Gly Lys Ile Ala Glu Cys
            115                 120                 125

Thr Phe Thr Lys Met Arg Ser Asn Ser Ala Leu Arg Val Leu Phe Ser
            130                 135                 140

Gly Ser Leu Arg Leu Lys Cys Arg Asn Ala Cys Cys Gln Arg Trp Tyr
145                 150                 155                 160

Phe Thr Phe Asn Gly Ala Glu Cys Ser Gly Pro Leu Pro Ile Glu Ala
            165                 170                 175

Ile Ile Tyr Leu Asp Gln Gly Ser Pro Glu Leu Asn Ser Thr Ile Asn
            180                 185                 190

Ile His Arg Thr Ser Ser Val Glu Gly Leu Cys Glu Gly Ile Gly Ala
            195                 200                 205

Gly Leu Val Asp Val Ala Ile Trp Val Gly Thr Cys Ser Asp Tyr Pro
            210                 215                 220

Lys Gly Asp Ala Ser Thr Gly Trp Asn Ser Val Ser Arg Ile Ile Ile
225                 230                 235                 240

Glu Glu Leu Pro Lys
            245
```

```
<210> SEQ ID NO 14
<211> LENGTH: 198
<212> TYPE: PRT
<213> ORGANISM: Pan troglodytes

<400> SEQUENCE: 14

Met Arg Pro Gln Gly Pro Ala Ala Ser Pro Gln Arg Leu Arg Gly Leu
1               5                   10                  15

Leu Leu Leu Leu Leu Gln Leu Pro Ala Pro Ser Ser Ala Ser Glu
            20                  25                  30

Ile Pro Lys Gly Lys Gln Lys Ala Gln Leu Arg Gln Arg Glu Val Val
            35                  40                  45

Asp Leu Tyr Asn Gly Met Cys Leu Gln Gly Pro Ala Gly Val Pro Gly
        50                  55                  60

Arg Asp Gly Ser Pro Gly Ala Asn Gly Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
            115                 120                 125

Thr Lys Met Arg Ser Asn Ser Ala Leu Arg Val Leu Phe Ser Gly Ser
130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Gly Met
            195

<210> SEQ ID NO 15
<211> LENGTH: 243
<212> TYPE: PRT
<213> ORGANISM: Macaca mulatta

<400> SEQUENCE: 15

Met Arg Pro Gln Gly Pro Ala Ala Ser Pro Gln Arg Leu Arg Gly Leu
1               5                   10                  15

Leu Leu Leu Leu Leu Gln Leu Pro Ala Pro Ser Ser Ala Ser Glu
            20                  25                  30

Ile Pro Lys Gly Lys Gln Lys Ala Gln Leu Arg Gln Arg Glu Val Val
            35                  40                  45

Asp Leu Tyr Asn Gly Met Cys Leu Gln Gly Pro Ala Gly Val Pro Gly
        50                  55                  60

Arg Asp Gly Ser Pro Gly Ala Asn Gly Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Val Glu Cys Thr Phe
            115                 120                 125

Thr Lys Met Arg Ser Asn Ser Ala Leu Arg Val Leu Phe Ser Gly Ser
```

```
                         130                 135                 140
Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val Glu Gly Leu Cys Glu Gly Ile Gly Ala Gly Leu
        195                 200                 205

Val Asp Val Ala Ile Trp Val Gly Thr Cys Ser Asp Tyr Pro Lys Gly
    210                 215                 220

Asp Ala Ser Thr Gly Trp Asn Ser Val Ser Arg Ile Ile Ile Glu Glu
225                 230                 235                 240

Leu Pro Lys

<210> SEQ ID NO 16
<211> LENGTH: 732
<212> TYPE: DNA
<213> ORGANISM: Homo sapiens

<400> SEQUENCE: 16
atgcgacccc agggccccgc cgcctccccg cagcggctcc gcggcctcct gctgctcctg      60
ctgctgcagc tgcccgcgcc gtcgagcgcc tctgagatcc caaggggaa gcaaaaggcg     120 cagctccggc agagggaggt ggtggacctg tataatggaa tgtgcttaca agggccagca    180
ggagtgcctg gtcgagacgg gagccctggg gccaatgtta ttccgggtac acctgggatc    240
ccaggtcggg atggattcaa aggagaaaag ggggaatgtc tgagggaaag ctttgaggag    300
tcctggacac ccaactacaa gcagtgttca tggagttcat tgaattatgg catagatctt    360
gggaaaattg cggagtgtac atttacaaag atgcgttcaa atagtgctct aagagttttg    420
ttcagtggct cacttcggct aaaatgcaga atgcatgct gtcagcgttg gtatttcaca     480
ttcaatggag ctgaatgttc aggacctctt cccattgaag ctataattta tttggaccaa   540
ggaagccctg aaatgaattc aacaattaat attcatcgca cttcttctgt ggaaggactt    600
tgtgaaggaa ttggtgctgg attagtggat gttgctatct gggttggcac ttgttcagat    660
tacccaaaag gagatgcttc tactggatgg aattcagttt ctcgcatcat tattgaagaa    720
ctaccaaaat aa                                                        732

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
1               5
```